United States Patent
Min

(10) Patent No.: US 11,097,116 B2
(45) Date of Patent: Aug. 24, 2021

(54) SYSTEMS AND METHODS FOR PERFORMING CARDIAC RESYNCHRONIZATION THERAPY (CRT) USING LEADLESS PACEMAKERS

(71) Applicant: Pacesetter, Inc., Sylmar, CA (US)

(72) Inventor: Xiaoyi Min, Santa Rosa Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 278 days.

(21) Appl. No.: 16/422,671

(22) Filed: May 24, 2019

(65) Prior Publication Data

US 2020/0368538 A1 Nov. 26, 2020

(51) Int. Cl.
  *A61N 1/375* (2006.01)
  *A61N 1/362* (2006.01)
  (Continued)

(52) U.S. Cl.
  CPC ......... *A61N 1/3756* (2013.01); *A61N 1/3627* (2013.01); *A61N 1/3682* (2013.01);
  (Continued)

(58) Field of Classification Search
  CPC ................ A61N 1/3756; A61N 1/3627; A61N 1/36592; A61N 1/3682; A61N 1/3684;
  (Continued)

(56) References Cited

U.S. PATENT DOCUMENTS

| 8,265,738 B1 | 9/2012 | Min et al. |
| 2005/0125041 A1 | 6/2005 | Min et al. |

(Continued)

FOREIGN PATENT DOCUMENTS

| EP | 2526999 A1 | 11/2012 |
| WO | WO2013/080038 A2 | 6/2013 |
| WO | WO2014/178035 A1 | 11/2014 |

OTHER PUBLICATIONS

Min, X., et al. Comparison of P Wave Durations as Assessed with the Bipolar and Unipolar Atrial Intracardiac Electrograms: Applicability to QuickOptTM, Computers in Cardiology, pp. 773-776. (10-207).

(Continued)

*Primary Examiner* — Paula J Stice
(74) *Attorney, Agent, or Firm* — Vierra Magen Marcus LLP

(57) ABSTRACT

Embodiments of the present technology described herein are directed to implantable systems for performing cardiac resynchronization therapy (CRT), methods for use therewith, and leadless pacemakers for use therewith. Such a system can include a first leadless pacemaker configured to be implanted in or on the right atrial (RA) chamber and selectively pace the RA chamber, a second leadless pacemaker configured to be implanted in or on the right ventricular (RV) chamber and selectively pace the RV chamber, and a third leadless pacemaker configured to be implanted in or on the left ventricular (LV) chamber and selectively pace the LV chamber, wherein one of the leadless pacemaker is designated a master leadless pacemaker. In certain embodiments, the master leadless pacemaker determines a VV delay and an AV delay and coordinates CRT using such delays.

21 Claims, 12 Drawing Sheets

(51) Int. Cl.
  *A61N 1/368*   (2006.01)
  *A61N 1/365*   (2006.01)
  *A61N 1/05*    (2006.01)
  *A61N 1/39*    (2006.01)
  *A61B 5/352*   (2021.01)

(52) U.S. Cl.
  CPC ....... *A61N 1/3684* (2013.01); *A61N 1/36592* (2013.01); *A61B 5/352* (2021.01); *A61N 1/056* (2013.01); *A61N 1/3622* (2013.01); *A61N 1/36542* (2013.01); *A61N 1/3962* (2013.01)

(58) Field of Classification Search
  CPC ... A61N 1/056; A61N 1/3622; A61N 1/36542
  See application file for complete search history.

(56) References Cited

U.S. PATENT DOCUMENTS

| | | |
|---|---|---|
| 2010/0114232 A1 | 5/2010 | Min |
| 2013/0238045 A1 | 9/2013 | Blomqvist et al. |
| 2016/0067501 A1 | 3/2016 | Xi et al. |
| 2016/0121128 A1 | 5/2016 | Fishler et al. |

OTHER PUBLICATIONS

European Extended Search Report dated Oct. 29, 2020, European Patent Application No. 20171556.2-1122.

SYSTEMS AND METHODS FOR PERFORMING CARDIAC RESYNCHRONIZATION THERAPY (CRT) USING LEADLESS PACEMAKERS

FIELD OF TECHNOLOGY

Embodiments of the present technology generally relate to methods, systems and devices that can be used to provide Cardiac Resynchronization Therapy (CRT), and can be used to select CRT parameters.

BACKGROUND

Heart failure (HF) is a debilitating, end-stage disease in which abnormal function of the heart leads to inadequate blood flow to fulfill the needs of the body's tissues. Typically, the heart loses propulsive power because the cardiac muscle loses capacity to stretch and contract. Often, the ventricles do not adequately fill with blood between heartbeats and the valves regulating blood flow may become leaky, allowing regurgitation or backflow of blood. The impairment of arterial circulation deprives vital organs of oxygen and nutrients. Fatigue, weakness, and inability to carry out daily tasks may result.

Not all HF patients suffer debilitating symptoms immediately. Some may live actively for years. Yet, with few exceptions, the disease is relentlessly progressive. As HF progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output.

Some treatments for HF are centered around medical treatment using ACE inhibitors, diuretics and/or digitalis. It has also been demonstrated that aerobic exercise may improve exercise tolerance, improve quality of life, and decrease symptoms. Cardiac surgery has also been performed on a small percentage of patients with particular etiologies. Although advances in pharmacological therapy have significantly improved the survival rate and quality of life of patients, some HF patients are refractory to drug therapy, have a poor prognosis and limited exercise tolerance. In recent years cardiac pacing, in particular Cardiac Resynchronization Therapy (CRT), has emerged as an effective treatment for many patients with drug-refractory HF.

While CRT does not work for all HF patients, a majority of HF patients are CRT responders, meaning that CRT can be used to improve those patients' HF condition. CRT pacing parameters are preferably individualized for patients to increase CRT benefits.

While echocardiography based techniques are sometimes used to select CRT pacing parameters, echocardiography based CRT pacing parameter selection is very time consuming and poorly reproducible. Device based CRT parameter selection algorithms have alternatively been used to select CRT pacing parameters, including atrioventricular (AV) delay and interventricular (VV) delay. For example, St. Jude Medical's QuickOpt™ algorithm can be used to select AV and VV delays based on measures from an intra-cardiac electrogram (IEGM) or electrocardiogram (ECG), such as P-wave width, which is also known as P-wave duration.

CRT is conventionally performed using a conventional pacemaker that is implanted in a pectoral region of a patient. The pacemaker typically includes a housing (also known as a "can" or "case") from which extend three leads implanted into a patient's heart for delivering multi-chamber cardiac pacing and sensing. The three leads can include a right atrial (RA) lead, a right ventricular (RV) lead, and a left ventricular (LV) lead. The RA lead can be used to provide atrial chamber pacing stimulation and sensing and may include, for example, an atrial tip electrode and an atrial ring electrode implanted in the atrial appendage. The RV lead may include, for example, a ventricular tip electrode, a RV ring electrode, a RV coil electrode, and a superior vena cava (SVC) coil electrode. Typically, the RV lead is transvenously inserted into the heart so as to place the RV coil electrode in the RV apex, and the SVC coil electrode in the superior vena cava. Accordingly, the RV lead is capable of receiving cardiac signals, and delivering stimulation in the form of pacing (and potentially shock therapy) to the right ventricle (also referred to as the RV chamber). The LV lead can be used to sense left atrial and ventricular cardiac signals and to provide left chamber pacing therapy. The LV lead can be a multi-pole LV lead designed for placement in the "CS region" via the CS os for positioning a distal electrode adjacent to the left ventricle and/or additional electrode(s) adjacent to the left atrium (also referred to as the LA chamber). As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. An example of an LV lead is the Quartet™ quadripolar LV lead available from Abbott Cardiovascular (headquartered in St. Paul, Minn.).

When a conventional pacemaker is used to perform CRT, a controller (e.g., processor) that is located within the housing of the pacemaker can obtain sensed signals from electrodes of all three of the leads physically connected to the pacemaker. Further, the controller (e.g., processor) that is located within the housing of the pacemaker can provide instructions to one or more pulse generators and electrode configuration switches to control the timing and stimulation vectors used to deliver cardia therapy.

Recently there has been an increased interest in using leadless pacemakers (LPs) to deliver cardiac therapy. LPs offer an alternative to traditional pacemakers by eliminating the need for transvenous leads. Further, LPs do not require a creation of a surgical pocket on the chest. When an LP is in place, there is no lump under the skin on the chest or leads anchored to the muscle bed, Further, LPs avoid certain complications associated with conventional pacemakers, including pocket complications such as pocket hematoma, infection, erosion, migration of the pacemaker, and Twiddler's syndrome. Additionally, LPs avoid lead-related complications such as lead dislodgement, pneumothorax, loose connector pin, conductor coil (lead) fracture, and insulation break.

LPs have been successfully implanted in the right ventricle (RV) chamber of patients to provide single chamber sensing and pacing. Dual chamber LP systems have also been proposed wherein a first LP is implanted in the RV chamber and a second LP is implanted in the RA chamber to provide for dual chamber pacing. Depending upon the specific type of pacing needed, where a patient includes LPs implanted in the RA and RV chambers, the two LPs need to communicate with one another to provide appropriate timed atrioventricular (AV) delays. Implant-to-implant (i2i) communications can be used by the two LPs to communicate with one another to achieve desired AV synchrony.

Since leadless pacemaker (LP) systems provide certain benefits over conventional pacemaker systems that include leads, it would be beneficial if LP systems could be used to perform CRT. An LP system that is capable of performing CRT may include three LPs, including an LP capable of pacing the RV chamber, an LP capable of pacing the LV chamber, and an LP capable of pacing the RA chamber. However, in contrast to conventional pacemakers, LP systems do not include a single controller (e.g., processor) located within the housing of the pacemaker to obtain sensed signals from electrodes of three leads physically connected to the pacemaker. Further, in contrast to conventional pacemakers, LP systems do not include a single controller (e.g., processor) located within the housing of the pacemaker that provides instructions to pulse generators and electrode configuration switches within the housing of the pacemaker to control the timing and stimulation vectors used to deliver cardia therapy. Accordingly there is a need to provide LP systems, and methods for use therewith, that can perform CRT using three physically separated LPs.

SUMMARY

Certain embodiments of the present technology are related to methods for performing cardiac resynchronization therapy (CRT) using an implantable leadless pacemaker system including a first leadless pacemaker (LP1) implanted in or on the right atrial (RA) chamber, a second leadless pacemaker (LP2) implanted in or on the right ventricular (RV) chamber, and a third leadless pacemaker (LP3) implanted in or on the left ventricular (LV) chamber, wherein one of the LP1, the LP2, or the LP3 is designated a master LP. For example, in certain embodiments, the LP2 that is implanted in or on the RV chamber is designated the master.

In accordance with certain embodiments, a method includes the LP1, which is implanted in or on the RA chamber, measuring a P-wave duration based on a signal sensed by the LP1. The LP1, which is implanted in or on the RA chamber, or another one of the LPs that is designated the master LP, determines an atrio-ventricular (AV) delay based on the measured P-wave duration. The LP2, which is implanted in or on the RV chamber, or another one of the LPs that is designated the master LP, determines a first AR or PR interval indicative of a time between an atrial depolarization and a ventricular depolarization in the RV chamber. The LP3, which is implanted in or on the LV chamber, or another one of the LPs that is designated the master LP, determines a second AR or PR interval indicative of a time between an atrial depolarization and a ventricular depolarization in the LV chamber. When determining the first and second PR intervals, the time at which an atrial depolarization is considered to occur can be, e.g., a beginning, a peak, or an end a P-wave (so long as this is done consistently for both the first and second PR intervals); and the time at which a ventricular depolarization is considered to occur is preferably when a peak of an R-wave or QRS complex occurs. In other words, where an atrial event (i.e., an atrial depolarization) is sensed, a time at which the atrial event is considered to occur can be, e.g., at a beginning, a peak, or an end of a P-wave, so long as the way this is achieved is consistent. Preferably, the time at which a ventricular event is considered to occur in the RV chamber is at a peak of an R-wave or QRS complex of an EGM indicative of electrical activity in the RV chamber, and a time at which a ventricular event is considered to occur in the LV chamber is at a peak of an R-wave or ORS complex of an EGM indicative of electrical activity in the LV chamber.

The one of the LPs that is designated the master LP determines a delta indicative of a difference between the first AR or PR interval and the second AR or PR interval. The LP2, which is implanted in or on the RV chamber, paces the RV chamber, and at least one of the LPs determines an RV-LV delay indicative of a time it takes for a ventricular depolarization in the RV chamber to propagate to the LV chamber. The LP3, which is implanted in or on the LV chamber, paces the LV chamber, and at least one of the LPs determines an LV-RV delay indicative of a time it takes for a ventricular depolarization in the LV chamber to propagate to the RV chamber. The method also includes the one of the LPs that is designated the master LP determining a correction factor indicative of a difference between the LV-RV delay and the RV-LV delay, and determining a VV delay based on the determined delta and the determined correction factor. The LP1, the LP2, and the LP3 collectively perform CRT using the determined AV delay and the determined VV delay.

In accordance with certain embodiments, the measuring the P-wave duration occurs during a first set of cardiac cycles comprising one or more cardiac cycles; the determining the first AR or PR interval during a second set of cardiac cycles comprising one or more cardiac cycles that may or may not overlap with the first set of cardiac cycles; the determining the second AR or PR interval occurs during a third set of cardiac cycles comprising one or more cardiac cycles that may or may not overlap with the first and/or second set of cardiac cycles; the pacing the RV chamber and the determining the RV-LV delay occurs during a fourth set of cardiac cycles comprising one or more cardiac cycles that do not overlap with any of the first, second, and third sets of cardiac cycles; and the pacing the LV chamber and the determining the LV-RV delay occurs during a fifth set of cardiac cycles comprising one or more cardiac cycles that do not overlap with any of the first, second, third, and fourth sets of cardiac cycles.

In accordance with certain embodiments, when the AV delay is for use in pacing during one or more cardiac cycles that start with an intrinsic atrial event, the determining the AV delay based on the measured P-wave duration, comprises: setting the AV delay to the P-wave duration plus a first offset, in response to the P-wave duration being greater than a threshold duration; and setting the AV delay to the P-wave duration plus a second offset that is greater than the first offset, in response to the P-wave duration being less than the threshold duration. It is also within the scope of the embodiments described herein to use some other measure of inter-atrial conduction delay (IACD), besides P-wave duration, to determine the AV delay.

In accordance with certain embodiments, when the AV delay is for use in pacing during one or more cardiac cycles that start with a paced atrial event, the determining the AV delay based on the measured P-wave duration, comprises: setting the AV delay to the P-wave duration plus a third offset, in response to the P-wave duration being greater than a second threshold duration; and setting the AV delay to the P-wave duration plus a fourth offset that is greater than the third offset, in response to the P-wave duration being less than the second threshold duration.

In accordance with certain embodiments, the one of the LPs that is designated the master LP determines the VV delay as being equal to half of a sum of the determined delta plus the determined correction factor.

In accordance with certain embodiments, the LP1, the LP2, and the LP3 collectively performing CRT using the determined AV delay and the determined VV delay, comprises: the LP2, determining on its own or based on an i2i message received from the LP1, when an atrial paced or sensed event occurs; and the LP3, determining on its own or based on an i2i message received from the LP1, when the atrial paced or sensed event occurs. If the VV delay is negative, then the LP3 can pace the LV chamber at the AV delay following when the atrial paced or sensed event occurs, and then the LP2 can pace the RV chamber at the VV delay following when the LP3 paces the LV chamber; and if the VV delay is positive, then the LP2 can pace the RV chamber at the AV delay following when the atrial paced or sensed event occurs, and then the LP3 can pace the LV chamber at the VV delay following when the LP2 paces the RV chamber. Alternatively, if the VV delay is negative, then the LP3 can pace the LV chamber at the AV delay following when the atrial paced or sensed event occurs, and then the LP2 can pace the RV chamber at a delay equal to a sum of the AV delay plus the VV delay following when the atrial paced or sensed event occurs; and if the VV delay is positive, then the LP2 can pace the RV chamber at the AV delay following when the atrial paced or sensed event occurs, and then the LP3 can pace the LV chamber at the delay equal to a sum of the AV delay plus the VV delay following when the atrial paced or sensed event occurs.

In accordance with certain embodiments, the method further includes the LP1 pacing the RA chamber at a VA delay following when the LP2 paces the RV chamber or the LP3 paces the LV chamber.

Certain embodiments of the present technology are related to implantable systems for performing CRT. Such a system can include a first leadless pacemaker (LP1) configured to be implanted in or on the RA chamber and selectively pace the RA chamber; a second leadless pacemaker (LP2) configured to be implanted in or on the RV chamber and selectively pace the RV chamber; and a third leadless pacemaker (LP3) configured to be implanted in or on the LV chamber and selectively pace the LV chamber, wherein one of the LPI, the LP2, or the LP3 is designated a master LP. The LP1 is also configured to sense a signal and measure a P-wave duration based on the signal sensed by the LP1. The LP1, or another one of the LPs that is designated the master LP, is configured to determine an AV delay based on the measured P-wave duration. The LP2, or another one of the LPs that is designated the master LP, is configured to determine a first AR or PR interval indicative of a time between an atrial depolarization and a ventricular depolarization in the RV chamber. The LP3, or another one of the LPs that is designated the master LP, is configured to determine a second AR or PR interval indicative of a time between an atrial depolarization and a ventricular depolarization in the LV chamber. At least one of the LPs is configured to determine an RV-LV delay indicative of a time it takes for a ventricular depolarization in the RV chamber to propagate to the LV chamber in response to the LP2 pacing the RV chamber. In accordance with certain embodiments, a time at which a ventricular depolarization in the RV chamber is considered to have propagated to the LV chamber is at a peak of an R-wave or QRS complex detected by the LP3 implanted within the LV chamber. At least one of the LPs is configured to determine an LV-RV delay indicative of a time it takes for a ventricular depolarization in the LV chamber to propagate to the RV chamber in response to the LP3 pacing the LV chamber. In accordance with certain embodiments, a time at which a ventricular depolarization in the LV chamber is considered to have propagated to the RV chamber is at a peak of an R-wave or QRS complex detected by the LP2 implanted within the RV chamber. The one of the LPs that is designated the master LP is configured to determine a delta indicative of a difference between the first AR or PR interval and the second AR or PR interval, determine a correction factor indicative of a difference between the LV-RV delay and the RV-LV delay, and determine a VV delay based on the determined delta and the determined correction factor. The LP1, the LP2, and the LP3 are configured to collectively perform CRT using the determined AV delay and the determined VV delay.

In accordance with certain embodiments, the LP1, which is configured to be implanted in or on the RA chamber, is configured to measure the P-wave duration during a first set of cardiac cycles comprising one or more cardiac cycles; the LP2, which is configured to be implanted in or on the RV chamber, is configured to determine the first AR or PR interval during a second set of cardiac cycles comprising one or more cardiac cycles that may or may not overlap with the first set of cardiac cycles; the LP3, which is configured to be implanted in or on the LV chamber, is configured to determine the second AR or PR interval during a third set of cardiac cycles comprising one or more cardiac cycles that may or may not overlap with the first and/or second set of cardiac cycles; the LP2 is also configured to determine the RV-LV delay during a fourth set of cardiac cycles comprising one or more cardiac cycles that do not overlap with any of the first, second, and third sets of cardiac cycles; and the LP3 is also configured to determine the LV-RV delay during a fifth set of cardiac cycles comprising one or more cardiac cycles that do not overlap with any of the first, second, third, and fourth sets of cardiac cycles.

In accordance with certain embodiments, when the AV delay is for use in pacing during one or more cardiac cycles that start with an intrinsic atrial event, the LP that is designated the master is configured to: set the AV delay to the P-wave duration plus a first offset, in response to the P-wave duration being greater than a threshold duration; and set the AV delay to the P-wave duration plus a second offset that is greater than the first offset, in response to the P-wave duration being less than the threshold duration.

In accordance with certain embodiments, when the AV delay is for use in pacing during one or more cardiac cycles that start with a paced atrial event, the LP that is designated the master is configured to: set the AV delay to the P-wave duration plus a third offset, in response to the P-wave duration being greater than a second threshold duration; and set the AV delay to the P-wave duration plus a fourth offset that is greater than the third offset, in response to the P-wave duration being less than the second threshold duration.

In accordance with certain embodiments, the LP that is designated the master LP is configured to determine the VV delay as being equal to half of a sum of the determined delta plus the determined correction factor.

In accordance with certain embodiments, the LP1, the LP2, and the LP3 are configured to collectively performing CRT using the determined AV delay and the determined VV delay, and wherein: the LP2 is configured to determine on its own or based on an i2i message received from the LP1, when an atrial paced or sensed event occurs; and the LP3 is configured to determine on its own or based on an i2i message received from the LP1, when the atrial paced or sensed event occurs. When the VV delay is negative, the LP3 is configured to pace the LV chamber at the AV delay following when the atrial paced or sensed event occurs, and the LP2 is configured to pace the RV chamber at the VV delay following when the LP3 paces the LV chamber. When the VV delay is positive, the LP2 is configured to pace the RV chamber at the AV delay following when the atrial paced or sensed event occurs, and the LP3 is configured to pace the LV chamber at the VV delay following when the LP2 paces the RV chamber.

In accordance with certain embodiments, the one of the LPs that is designated the master LP is configured to orchestrate the CRT that is collectively performed by the LP1, the LP2, and the LP3 using the determined AV delay and the determined VV delay.

In accordance with certain embodiments, the LP1, which is configured to be implanted in or on the RA chamber, is configured to pace the RA chamber at a VA delay following when the LP2 paces the RV chamber or the LP3 paces the LV chamber.

In accordance with certain embodiments, the LP2, which is configured to be implanted in or on the RV chamber, is designated the master LP.

Certain embodiments of the present technology are directed to a leadless pacemaker (rvLP) configured to be implanted in or on a right ventricular (RV) chamber and configured to perform cardiac resynchronization therapy (CRT) along with a leadless pacemaker (raLP) configured to be implanted in or on a right atrial (RA) chamber and a leadless pacemaker (lvLP) configured to be implanted in or on the left ventricular (LV) chamber. In such embodiments, the rvLP comprises one or more pulse generators, a plurality of electrodes, and a controller. The one or more pulse generators is/are configured to selectively produce pacing pulses and implant-to-implant (i2i) communication pulses, the pacing pulses for use in pacing the RV chamber, and the i2i communication pulses for use in sending i2i messages to at least one of the raLP or the lvLP. At least two of the electrodes can be used to deliver one or more pacing pulses to the RV chamber; at least two of the electrodes can be used to transmit and receive one or more i2i communication pulses to and from at least one of the raLP or the lvLP; and at least two of the electrodes can be used to sense a far-field signal from which cardiac activity associated with at least one of the RA or LV chambers may be detected. The controller is configured to determine: an atrio-ventricular (AV) delay based on a P-wave duration measurement received via one or more i2i communication pulses from the raLP; an RV-LV delay indicative of a time it takes for a ventricular depolarization in the RV chamber to propagate to the LV chamber in response to the rvLP pacing the RV chamber; an LV-RV delay indicative of a time it takes for a ventricular depolarization in the LV chamber to propagate to the RV chamber in response to the lvLP pacing the LV chamber; a delta indicative of a difference between a first AR or PR interval and a second AR or PR interval; a correction factor indicative of a difference between the LV-RV delay and the RV-LV delay; and a VV delay based on the determined delta and the determined correction factor. The controller is also configured to coordinate performance of CRT collectively by the rvLP, the raLP, and the lvLP using the determined AV delay and the determined VV delay, as well as using a VA delay.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Figure 1A:
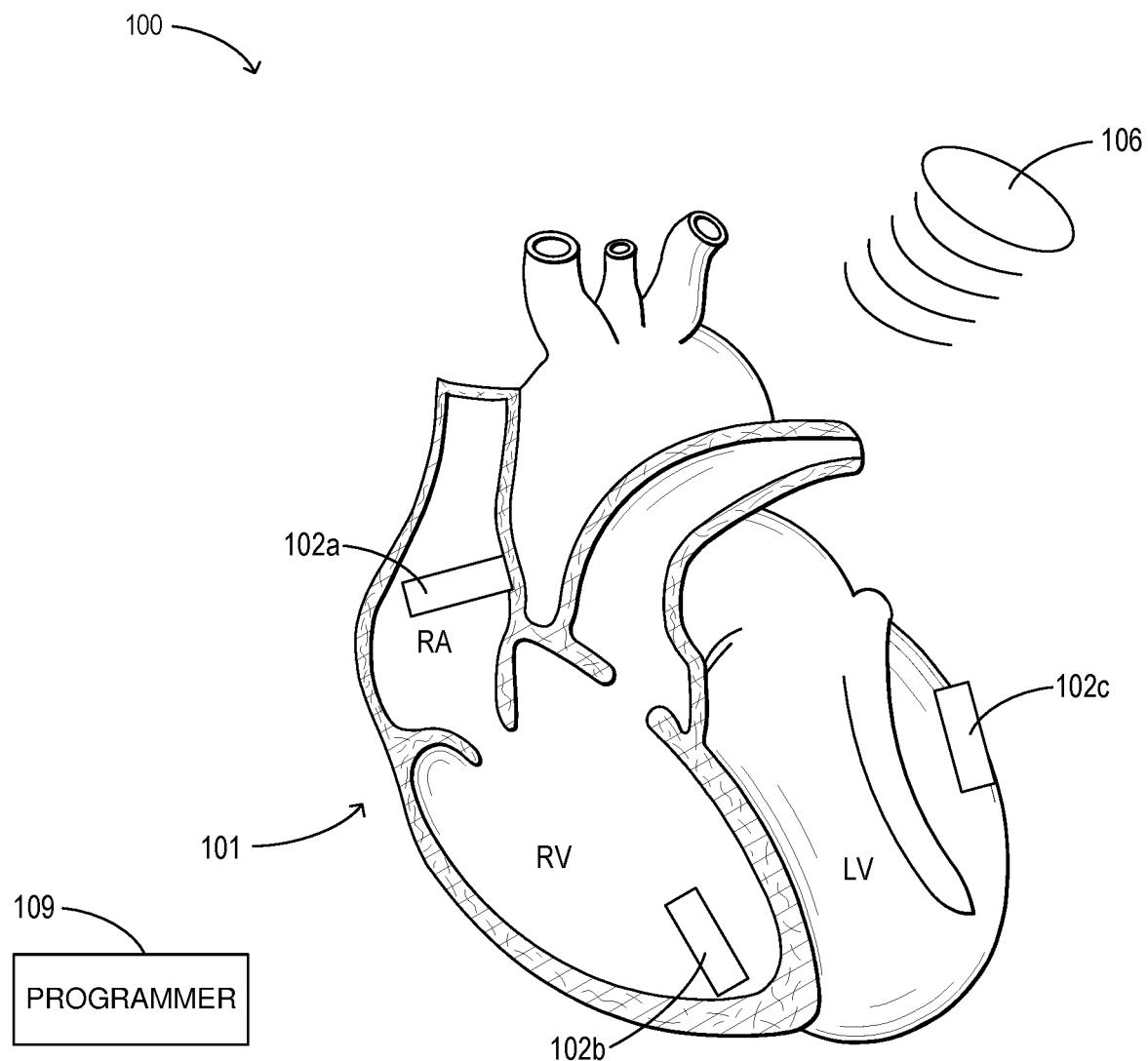
FIG. 1A illustrates a system formed in accordance with certain embodiments described herein as implanted in and/or on a heart.

Certain embodiments of the present technology relate to implantable systems, and methods for use therewith, that can be used to perform cardiac synchronization therapy (CRT). For example, certain embodiments of the present technology relate to implantable systems, and methods for use therewith, that can be used perform DDD or DDI pacing using three LPs, wherein one of the LPs (LP1) is implanted in (or on) a patient's RA chamber, one of the LPs (LP2) is implanted in (or on) the patient's RV chamber, and one of the LPs (LP3) is implanted in (or on) the patient's LA chamber. More specifically, in accordance with certain embodiments of the present technology, the LP1 implanted in (or on) a patient's RA chamber and is used to perform ADD pacing, the LP2 implanted in (or on) the patient's RV chamber is used to perform VDD pacing, and the LP3 implanted in (or on) the patient's LV chamber is used to perform VDD pacing. Collectively, the LP1, the LP2, and the LP3 in such an embodiment performs DDD or DDI pacing or some other tri-chamber pacing mode that provides synchronization between the LP1, the LP2, and the LP3. Where LPs are said to be synchronized or have synchronization provided, this means that the pacing performed by at least one of the LPs is timed relative to paced events delivered by and/or sensed events sensed by the other LPs. Accordingly, two LPs can be said to be synchronized where there is VA synchrony but not AV synchrony, VA synchrony but not AV synchrony, or both VA and AV synchrony Any one of various different algorithms can be used to achieve such dual chamber pacing modes. When referring to various types of pacing schemes herein, three letters are often used to refer to the type of pacing. In other words, a three position pacemaker code is often used, with the following nomenclature followed: the first position refers to the cardiac chamber paced; the second position refers to the cardiac chamber sensed; and the third position refers to the response to a sensed event. In the first and second positions, the letter O means none, the letter A means Atrium, the letter V means Ventricle, and the letter D means Dual (i.e., A and V). In the third position the letter O means none, the letter I means Inhibited, the letter T means Triggered (aka Tracked), and the letter D means Dual (i.e., T+I). The below Table 1 summarizes this pacemaker nomenclature.

TABLE 1

| Position 1 (Chamber Paced) | Position 2 (Chamber Sensed) | Position 3 (Response to Sensed Event) |
| --- | --- | --- |
| O = none | O = none | O = none |
| A = Atrium | A = Atrium | I = Inhibited |
| V = Ventricle | V = Ventricle | T = Triggered (aka Tracked) |
| D = Dual (A + V) | D = Dual (A + V) | D = Dual (I + T) |

Accordingly, if an LP in the patient's RV chamber performs VDD pacing, that means it paces only the RV chamber, senses both atrial and ventricular activity, and inhibits pacing of the RV if a sensed event is detected within a specified interval (the AV interval) or triggers pacing of the RV at the end of the specified interval (the AV interval) if a sensed event is not detected within that specified interval (the AV interval). For another example, if an LP in the patient's RA chamber performs AAI pacing, that means it paces only the RA chamber, senses only atrial activity, and inhibits pacing of the RA chamber if a sensed event is detected within a specified interval. Where the second position includes a "D", the LP will need to be aware of activity in its own chamber and in another chamber in or one which the LP is not implanted. Activity in another chamber can be determined from a far-field signal and/or from an i2i message received from another LP that is in or one the other chamber.

When an LP in (or on) the RV or LV chamber performs VDD pacing, it should know when certain cardiac activity (e.g., atrial contractions) occur in the RA chamber, so that it knows the appropriate times at which to pace the RV or LV chamber.

Before providing addition details of the specific embodiments of the present technology mentioned above, as well as additional embodiments of the present technology, an exemplary system in which embodiments of the present technology can be used will first be described with reference to FIGS. 1A, 1B, and 2. More specifically, FIGS. 1A, 1B, and 2 will be used to describe an exemplary cardiac pacing system, wherein pacing and sensing operations can be performed by multiple medical devices, which include three LPs, an optional implantable cardioverter-defibrillator (ICD), such as a subcutaneous-ICD, and/or a programmer reliably and safely coordinate pacing and/or sensing operations. In certain embodiments, described in more detail below, one of the LPs is designated the master LP, with the other two LPs being slave LPs.

FIG. 1A illustrates a system 100 formed in accordance with certain embodiments herein as implanted in and/or on a heart 101. The system 100 comprises three LPs 102a, 102b and 102c located in or on different chambers of the heart. LP 102a is located in the RA chamber, while LP 102b is located in the RV chamber, and the LP 102c is located in the LV chamber. The LPs 102a, 102b, and 102c can be referred to collectively as the LPs 102, or individually as an LP 102. The LPs 102 can communicate with one another to inform one another of various local physiologic activities, such as local intrinsic events, local paced events and the like. The LPs 102a, 102b and 102c may be constructed in a similar manner, but operate differently based upon which chamber the LP is located. It is noted that the RA chamber is also known as the right atrium, and the acronym RA can be used to refer to the "right atrium" or to refer to the "right atrial" chamber. Similarly, the RV chamber is also known as the right ventricle, and the acronym RV can be used to refer to the "right ventricle" or to refer to the "right ventricular" chamber. Further, the LV chamber is also known as the left ventricle, and the acronym LV can be used to refer to the "left ventricle" or to refer to the "left ventricular" chamber. It is also noted that the terms "cardiac chamber", "chamber of the heart", and "chamber of a patient's heart" are used interchangeably herein.

In accordance with certain embodiments, the LP 102a is used to perform ADD pacing, each of the LPs 102b and 102c is used to perform VDD pacing, and the LPs 102a, 102b and 102c are collectively used to perform DDD pacing. The ADD pacing (performed by the LP 102a) involves atrial pacing, ventricular and atrial (i.e., dual) sensing, and dual (i.e., triggered and inhibited) response to a sensed event. The VDD pacing (performed by the LPs 102b and 102c) involves ventricular pacing, atrial and ventricular (i.e., dual) sensing, and dual (i.e., triggered and inhibited) response to a sensed event. The DDD pacing (performed collectively by the LPs 102a, 102b and 102c) involves atrial and ventricular (i.e., dual) pacing, atrial and ventricular (i.e., dual) sensing, and dual (i.e., triggered and inhibited) response to a sensed event.

In some embodiments, all (or at least some) of the LPs 102a, 102b and 102c communicate with one another, with an ICD 106, and with an external device (e.g., programmer) 109 through wireless transceivers, communication coils and antenna, and/or by conductive communication through the same electrodes as (or one or more different electrodes than) used for sensing and/or delivery of pacing therapy. When conductive communication is performed using electrodes, the system 100 may omit an antenna or telemetry coil in one or more of the LPs 102.

In some embodiments, one or more LPs 102 can be co-implanted with the ICD 106. Each LP 102 uses two or more electrodes located within, on, or within a few centimeters of the housing of the LP, for pacing and sensing at the cardiac chamber, for bidirectional communication with at least one other LP, the programmer 109 (or some other external device), and the ICD 106.

In FIG. 1A, the LPs 102a, 102b and 102c are shown as being implanted endocardially, i.e., within respective cardiac chambers. In other words, in FIG. 1A each of the LPs 102 is shown as being implanted in a respective cardiac chamber, i.e., the LP 102a is shown as being implanted in the RA chamber, the LP 102b is shown as being implanted in the RV chamber, and the LP 102c is shown as being implanted in the LV chamber. Alternatively, one or more of the LPs 102 can be implanted epicardially (on the external heart surface) by affixing to the exterior surface of the heart. For example, it would also be possible for the LP 102a to be affixed to an exterior surface of the RA chamber, in which case the LP 102a can be said to be implanted on (rather than in) the RA chamber. Similarly, it would also be possible for the LP 102b to be affixed to an exterior of the RV chamber, in which case the LP 102b can be said to be implanted on (rather than in) the RV chamber. Further, it would also be possible for the LP 102c to be affixed to an exterior of the LV chamber, in which case the LP 102c can be said to be implanted on (rather than in) the LV chamber. More specifically, the LP 102c can be affixed to an exterior of the LV chamber using a minimally invasive procedure such that the LP 102c is located within the pericardial sac. It would also be possible to implant the LP 102c in the coronary sinus proximate the LV chamber. Alternatively, if the LP 102c is made small enough, the LP 102c can be implanted through the great vein.

More generally, an LP 102 can either be implanted in or on the cardiac chamber that the LP is being used to pace. It is noted that the terms "implanted in," "implanted within," "located in," and "located within" are used interchangeably herein when referring to where a particular LP is implanted. Further, it is noted that the terms "located on" and "implanted on" are used interchangeably herein when referring to where a particular LP is implanted. The cardiac chamber within or on which a particular LP is implanted can be referred to as a "local chamber", while another chamber (within or on which the particular LP is not implanted) can be referred to as a "remote chamber".

In accordance with certain embodiments, methods are provided for coordinating operation between LPs located in or on different cardiac chambers of the heart. Some such methods can configure a local LP to receive communications from a remote LP through conductive communication. Some such methods rely on a local LP sensing a far-field signal and/or a sensor signal to itself monitor cardiac activity associated with a remote cardiac chamber.

Figure 1B:
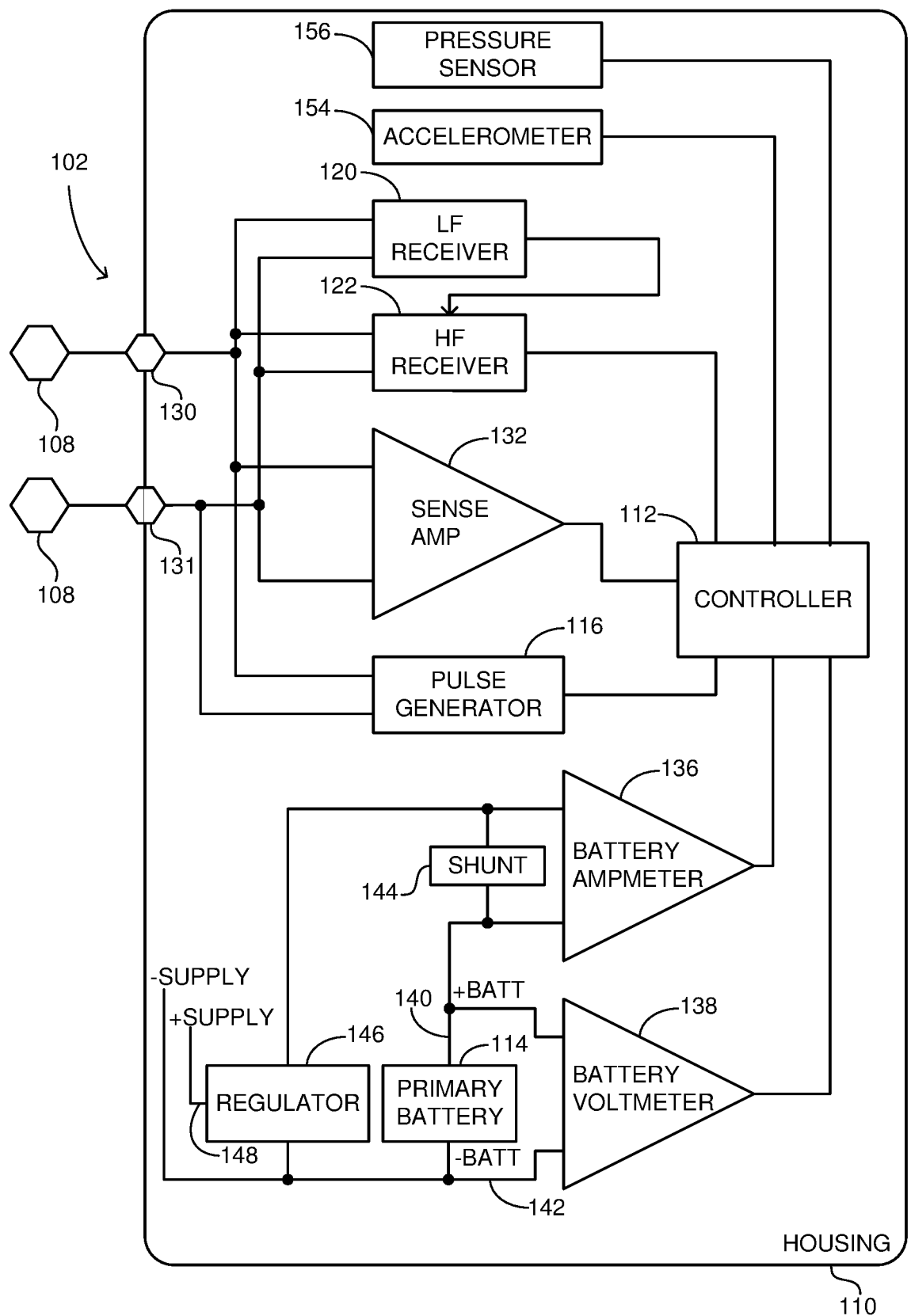
FIG. 1B is a block diagram of an exemplary leadless pacemaker (LP) in accordance with certain embodiments herein.

Referring to FIG. 1B, a block diagram shows exemplary electronics within an LP 102. The LP 102 includes first and second receivers 120 and 122 that collectively define separate first and second communication channels between LPs 102. Although first and second receivers 120 and 122 are depicted, in other embodiments, an LP 102 may only include first receiver 120, or may include additional receivers other than first and second receivers 120 and 122. As will be described in additional detail below, the pulse generator 116 can function as a transmitter that transmits implant-to-implant (i2i) communication signals using the electrodes 108. Usage of the electrodes 108 for communication enables the one or more LPs 102 to perform antenna-less and telemetry coil-less communication.

In accordance with certain embodiments, when one of the LPs 102 senses an intrinsic event or delivers a paced event, the corresponding LP 102 transmits an implant event message to one or more other LP(s) 102. For example, when an atrial LP 102 (102a) senses/paces an atrial event, the atrial LP 102 (102a) can transmit an implant event message including an event marker indicative of a nature of the event (e.g., intrinsic/sensed atrial event, paced atrial event). When a ventricular LP 102 (102b) senses/paces a ventricular event, the ventricular LP 102 (102b) transmits an implant event message including an event marker indicative of a nature of the event (e.g., intrinsic/sensed ventricular event, paced ventricular event). In certain embodiments, an LP 102 transmits an implant event message to at least one other LP 102 preceding the actual pace pulse so that the remote LP can blank its sense inputs in anticipation of that remote pace pulse (to prevent inappropriate crosstalk sensing). Where an implant event message is sent from one LP to another LP, the implant event message can be referred to as an implant-to-implant (i2i) event massage, or more generally, as an i2i message.

Still referring to FIG. 16, the LP 102 is shown as including a controller 112 and a pulse generator 116. The controller 112 can include, e.g., a microprocessor (or equivalent control circuitry), RAM and/or ROM memory, logic and timing circuitry, state machine circuitry, and I/O circuitry, but is not limited thereto. The controller 112 can further include, e.g., timing control circuitry to control the timing of the stimulation pulses (e.g., pacing rate, atrio-ventricular (AV) delay, atrial interconduction (A-A) delay, or ventricular interconduction (V-V) delay, etc.). Such timing control circuitry may also be used for the timing of refractory periods, blanking intervals, noise detection windows, evoked response windows, alert intervals, marker channel timing, and so on. The controller 112 can further include other dedicated circuitry and/or firmware/software components that assist in monitoring various conditions of the patient's heart and managing pacing therapies. The controller 112 and the pulse generator 116 may be configured to transmit event messages, via the electrodes 108, in a manner that does not inadvertently capture the heart in the chamber where LP 102 is located, such as when the associated chamber is not in a refractory state. In addition, an LP 102 that receives an event message may enter an "event refractory" state (or event blanking state) following receipt of the event message. The event refractory/blanking state may be set to extend for a determined period of time after receipt of an event message in order to avoid the receiving LP 102 from inadvertently sensing another signal as an event message that might otherwise cause retriggering. For example, the receiving LP 102 may detect a measurement pulse from another LP 102 or programmer 109.

In accordance with certain embodiments herein, the programmer 109 may communicate over a programmer-to-LP channel, with one or more of the LPs 102 utilizing the same communication scheme. The external programmer 109 may listen to the event message transmitted between LPs 102 and synchronize programmer to implant communication such that programmer 109 does not transmit communication signals until after an implant to implant messaging sequence is completed. Alternatively, the external programmer 109 may wait for a directed communication message transmitted to the external programmer 109 from an LP 102 that indicates to the external programmer 109 that the LP is ready to trade communication signals with the external programmer 109. An LP 102 can also communicate with other types of external devices besides the external programmer 109, such as, but not limited to, an external monitor.

In accordance with certain embodiments, an LP 102 may combine transmit operations with therapy. The transmit event marker may be configured to have similar characteristics in amplitude and pulse-width to a pacing pulse and an LP 102 may use the energy in the event messages to help capture the heart. For example, a pacing pulse may normally be delivered with pacing parameters of 2.5V amplitude, 500 ohm impedance, 60 bpm pacing rate, 0.4 ms pulse-width. The foregoing pacing parameters correspond to a current draw of about 1.9 µA. The same LP 102 may implement an event message utilizing event signaling parameters for amplitude, pulse-width, pulse rate, etc. that correspond to a current draw of approximately 0.5 µA for transmit.

An LP 102 may combine the event message transmissions with pacing pulses. For example, an LP 102 may use a 50 µs wakeup transmit pulse having an amplitude of 2.5V which would draw 250 nC (nano Coulombs) for an electrode load of 500 ohm. The pulses of the transmit event message may be followed by an event message encoded with a sequence of short duration pulses (for example 16, 2 µs on/off bits) which would draw an additional 80 nC. The event message pulse would then be followed by the remaining pulse-width needed to reach an equivalent charge of a nominal 0.4 ms pace pulse. In this case, the current necessary to transmit the marker is essentially free as it was used to achieve the necessary pace capture anyhow. With this method, the savings in transmit current could be budgeted for the receiver or would allow for additional longevity.

When an LP 102 senses an intrinsic event, it can send a qualitatively similar event pulse sequence (but indicative of a sensed event) without adding the pace pulse remainder. Where longevity calculations for an LP 102 are designed based on the assumption that the LP 102 will deliver pacing therapy 100% of the time, transmitting an intrinsic event marker to another LP 102 should not impact the nominal calculated LP longevity.

In some embodiments, the individual LP 102 can comprise a hermetic housing 110 configured for placement on or attachment to the inside or outside of a cardiac chamber and at least two leadless electrodes 108 proximal to the housing 110 and configured for bidirectional communication with at least one other device 106 within or outside the body. As will be described in additional detail below, with reference to FIGS. 5A and 5B, in certain embodiments an individual LP includes two hermetic housings, one of which includes electronic circuitry, and the other of which includes a battery.

Referring to FIG. 1B, the LP 102 is shown as including an accelerometer 154 which can be hermetically contained within the housing 110. The accelerometer 154 can be any one of various different types of well-known accelerometers, or can be a future developed accelerometer. For one example, the accelerometer 154 can be or include, e.g., a MEMS (micro-electromechanical system) multi-axis accelerometer of the type exploiting capacitive or optical cantilever beam techniques, or a piezoelectric accelerometer that employs the piezoelectric effect of certain materials to measure dynamic changes in mechanical variables. Where the accelerometer is a multi-axis accelerometer it can include two or three sensors aligned along orthogonal axes. Exemplary multi-axis accelerometers (also referred to as multi-dimensional accelerometers) that can be used are described in U.S. Pat. No. 6,658,292 (Kroll et al.) and U.S. Pat. No. 6,466,821 (Pianca et al.), each of which is incorporated herein by reference. For another example, a commercially available micro-electromechanical system (MEMS) accelerometer marketed as the ADXL345 by Analog Devices, Inc. (headquartered in Norwood, Mass.) is a three-axis accelerometer and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL345 includes a micro-machined accelerometer co-packaged with a signal processing IC.

Another commercially available MEMS accelerometer is the ADXL327 by Analog Devices, Inc., which is a small, thin, low power, complete three axis accelerometer with signal conditioned voltage outputs. In the ADXL327, the mechanical sensor and signal conditioning IC are packaged together. A further commercially available MEMS accelerometer that can be used is the LIS3DH three-axis accelerometer by STMicroelectronics (headquartered in Geneva, Switzerland). Additional and/or alternative types of accelerometers may also be used. For example, it is also within the scope of the present technology for the accelerometer 154 to be a beam-type of accelerometer, an example of which is described in U.S. Pat. No. 6,252,335 (Nilsson et al.), which is incorporated herein by reference.

The accelerometer 154 can be, e.g., a one-dimensional (1D) accelerometer (also known as a one-axis accelerometer), a two-dimensional (2D) accelerometer (also known as a two-axis accelerometer), or a three-dimensional (3D) accelerometer (also known as a three-axis accelerometer). A 1D accelerometer measures acceleration along one axis, e.g., the z-axis. A 2D accelerometer measures acceleration along two axes that are orthogonal to one another, e.g., the z-axis, and the x- or y-axis. A 3D accelerometer measures acceleration along three axes that are orthogonal to one another, e.g., the z-axis, the x-axis, and the y-axis. Each measure of acceleration (i.e., rate of change of velocity) can actually be a measure of proper acceleration, which is the rate of change of velocity of a body in its own instantaneous rest frame. For example, an accelerometer at rest on the surface of the Earth will measure an acceleration due to Earth's gravity, straight upwards (by definition) of g≈9.81 m/s^2.

Where an LP 102 includes an accelerometer within a housing of the LP or attached thereto, the accelerometer can be used to measure the acceleration of the LP along one or more axes, which measurement(s) can be used to determine the orientation of the LP. Accordingly, because the output(s) of the accelerometer can be used to determine the orientation of the LP, it can be said that the output(s) of the accelerometer (e.g., 154) are indicative of an orientation of the LP 102. More specifically, in accordance with certain embodiments, the controller 112 of an LP 102 receives one or more outputs output(s) of the accelerometer 154, which is/are indicative of an orientation of the LP 102. In such embodiments, the controller 112 can determine, based on the output(s) received from the accelerometer 154, an actual orientation of the LP 102. Each output of the accelerometer 154 can comprise a respective signal.

One or more signals produced and output by the accelerometer 154 may be analyzed with respect to frequency content, energy, duration, amplitude and/or other characteristics. Such signals may or may not be amplified and/or filtered prior to being analyzed. For example, filtering may be performed using lowpass, highpass and/or bandpass filters. The signals output by the accelerometer 154 can be analog signals, which can be analyzed in the analog domain, or can be converted to digital signals (by an analog-to-digital converter) and analyzed in the digital domain. Alternatively, the signals output by the accelerometer 154 can already be in the digital domain.

The one or more signals output by the accelerometer 154 can be analyzed by the controller 112 and/or other circuitry. In certain embodiments, the accelerometer 154 is packaged along with an integrated circuit (IC) that is designed to analyze the signal(s) it generates. In such embodiments, one or more outputs of the packaged sensor/IC can be an indication of acceleration along one or more axes. In other embodiments, the accelerometer 154 can be packaged along with an IC that performs signal conditioning (e.g., amplification and/or filtering), performs analog-to-digital conversions, and stores digital data (indicative of the sensor output) in memory (e.g., RAM, which may or may not be within the same package). In such embodiments, the controller 112 or other circuitry can read the digital data from the memory and analyze the digital data. Other variations are also possible, and within the scope of embodiments of the present technology. In accordance with certain embodiments of the present technology, described in additional detail below, a sensor signal produced by the accelerometer 154 of an LP implanted in or on a cardiac chamber can be used to detect mechanical cardiac activity associated with another cardiac chamber.

The LP 102 is also shown as including a pressure sensor 156. In accordance with certain embodiments, at least one of the accelerometer 154 of the pressure sensor 156, or some other sensor, such as a piezoelectric crystal, or a sensor including an acoustic diaphragm, can be used to sense sounds emitted from the patient's heart (also referred to as heart sounds) to provide a phonocardiogram (also known as a heart sound signal). Heart sounds are the noises generated by the beating heart and the resultant flow of blood, and are typically referred to as S1, S2, S3 and S4. Depending upon which heart sound is being detected, the LP1 can appropriately time its pacing therapy. The S1 heart sound, which is typically the loudest and most detectable of the heart sounds, is caused by the sudden block of reverse blood flow due to closure of the atrioventricular valves (mitral and tricuspid) at the beginning of ventricular contraction. Isovolumic relaxation (IR) occurs during ventricular diastole and is demarcated approximately by closure of the aortic valve and the second heart sound (S2) and approximately by opening of the mitral valve and the third heart sound (S3), which is more prominent in children and those with abnormal ventricular function when compared to normal adults. The onset of isovolumic relaxation time commences with aortic valve closure, which can be identified by the aortic component (A2) of the second heart sound (S2). The third heart sound (S3) has been linked to flow between the left atrium and the left ventricle, more generally LV filling, and thought to be due to cardiohemic vibrations powered by rapid deceleration of transmitral blood flow. The fourth heart sound (S4) may be present in the late stage of diastole and associated with atrial contraction, or kick, where the final 20% of the atrial output is delivered to the ventricles.

FIG. 1B depicts a single LP 102 and shows the LP's functional elements substantially enclosed in a hermetic housing 110. The LP 102 has at least two electrodes 108 located within, on, or near the housing 110, for delivering pacing pulses to and sensing electrical activity from the muscle of the cardiac chamber, and for bidirectional communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, receivers 120, 122 for receiving information from at least one other device via the electrodes 108, and the pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

In FIG. 1B, all of the components shown within the housing 110, besides the battery 114, can be referred generally as electrical circuitry or electronics of the LP 102. In FIG. 1B the battery 114 and the electronics are shown as being within the same housing 110. In certain embodiments of the present technology, described below with reference to FIGS. 5A and 5B, the battery 114 and the electronics are included within separate respective electrically conductive housings (e.g., 512 and 522 in FIG. 5A) that are electrically isolated from one another.

The electrodes 108 can be configured to communicate bidirectionally among the multiple LPs and/or the implanted ICD 106 to coordinate pacing pulse delivery and optionally other therapeutic or diagnostic features using messages that identify an event at an individual LP originating the message and an LP receiving the message react as directed by the message depending on the origin of the message. An LP 102 that receives the event message reacts as directed by the event message depending on the message origin or location. In some embodiments or conditions, the two or more leadless electrodes 108 can be configured to communicate bidirectionally among the one or more LPs 102 and/or the ICD 106 and transmit data including designated codes for events detected or created by an individual LP, Individual LPs can be configured to issue a unique code corresponding to an event type and a location of the sending pacemaker. While the LP 102 shown in FIG. 1B is shown as including only two electrodes 108, in alternative embodiments discussed below, an LP can include more than two electrodes.

In some embodiments, an individual LP 102 can be configured to deliver a pacing pulse with an event message encoded therein, with a code assigned according to pacemaker location and configured to transmit a message to one or more other LPs via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 102b may receive and relay an event message from LP 102a to the programmer. Similarly, information communicated on the outgoing channel can also include a message to another LP, or to the ICD, that the sending leadless cardiac pacemaker has sensed a heartbeat or has delivered a pacing pulse at the location of the sending pacemaker.

Referring again to FIG. 1A, the cardiac pacing system 100 may comprise an implantable cardioverter-defibrillator (ICD) 106 in addition to LPs 102 configured for implantation in electrical contact with a cardiac chamber and for performing cardiac rhythm management functions in combination with the implantable ICD 106. The implantable ICD 106 and the one or more LPs 102 can be configured for leadless intercommunication by information conduction through body tissue and/or wireless transmission between transmitters and receivers in accordance with the discussed herein.

As shown in the illustrative embodiments, an LP 102 can comprise two or more leadless electrodes 108 configured for delivering cardiac pacing pulses, sensing evoked and/or natural (i.e., intrinsic) cardiac electrical signals, and bidirectionally communicating with the co-implanted ICD 106.

LP 102 can be configured for operation in a particular location and a particular functionality at manufacture and/or at programming by an external programmer 109. Bidirectional communication among the multiple leadless cardiac pacemakers can be arranged to communicate notification of a sensed heartbeat or delivered pacing pulse event and encoding type and location of the event to another implanted pacemaker or pacemakers. LP 102 receiving the communication decode the information and respond depending on location of the receiving pacemaker and predetermined system functionality.

In some embodiments, the LPs 102 are configured to be implantable in any chamber of the heart, namely either atrium (RA, LA) or either ventricle (RV, LV). Furthermore, for multi-chamber configurations, multiple LPs may be co-implanted (e.g., one in the RA, one in the RV, and one in the LV or in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking and refractory periods, etc. Accordingly, each LP preferably knows an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or VVI), and for the IPG to utilize the proper set of settings and algorithms (e.g., V-AutoCapture vs. ACapConfirm, sensing sensitivities, etc.).

Also shown in FIG. 1B, the primary battery 114 has positive pole 140 and negative pole 142. Current from the positive pole 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the controller 112 with an indication of battery current drain and indirectly of device health. The illustrative power supply can be a primary battery 114.

In various embodiments, LP 102 can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in one LP 102 can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

In certain embodiments, the electrodes of an LP 102 can be used to sense an intracardiac electrocardiogram (IEGM) from which atrial and/or ventricular activity can be detected, e.g., by detecting R waves and/or P waves. Accordingly, the sensed IEGM can be used by an LP to time its delivery of pacing pulses. Where an IEGM sensed by an LP is indicative of electrical cardiac activity associated with the same cardiac chamber within or on which an LP is implanted, the IEGM can be referred to as a near-field signal. Where an IEGM sensed by an LP is indicative of electrical cardiac activity associate with another cardiac chamber of the heart (other than the cardiac chamber within or on which the LP is implanted), the IEGM can be referred to as a far-field signal. An IEGM can also be used by an LP 102 to time when i2i communication pulses should be generated and transmitted, since the orientation of the LPs 102 relative to one another can change throughout each cardiac cycle.

Figure 2:
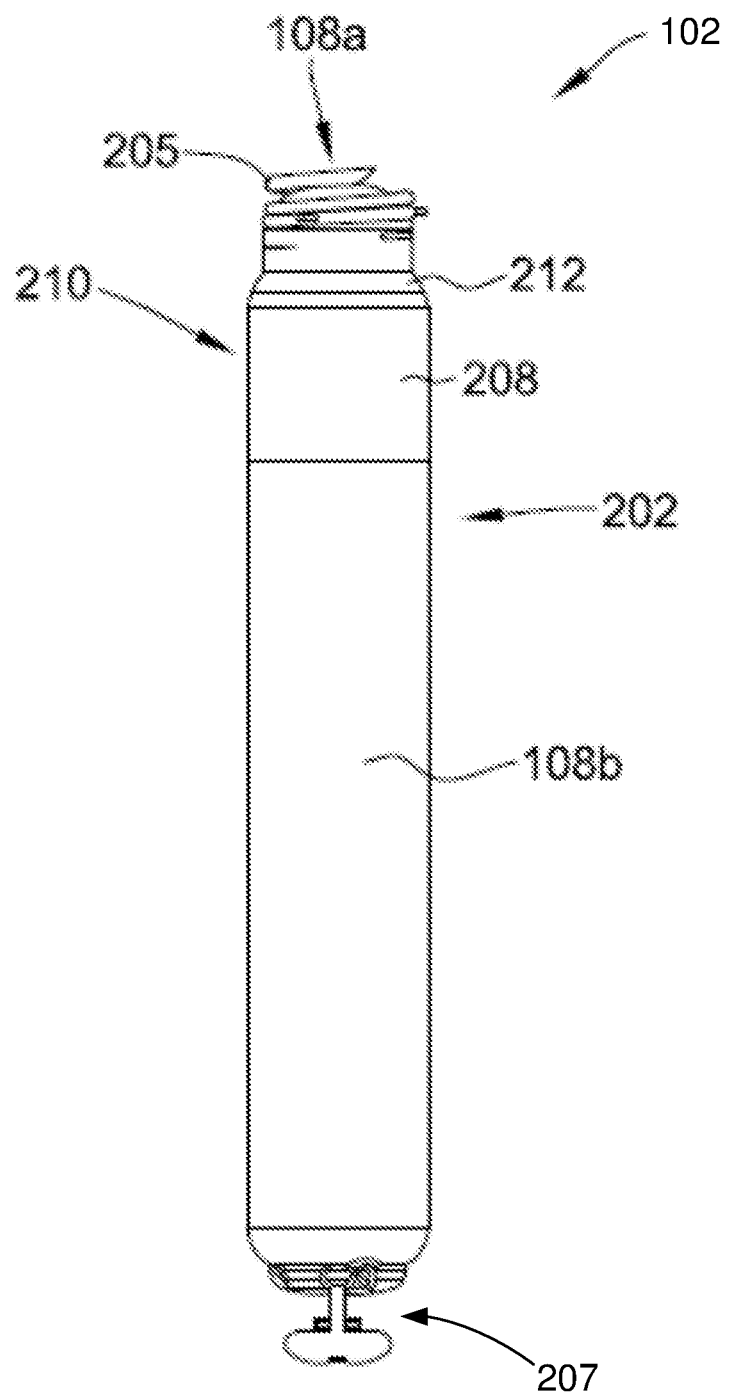
FIG. 2 illustrates an LP in accordance with certain embodiments herein.

FIG. 2 shows an LP 102. The LP can include a hermetic housing 202 (e.g., the housing 110 in FIG. 1) with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue. The electrodes 108a and 108b are examples of the electrodes 108 shown in and discussed above with reference to FIG. 1B. One of the electrodes 108 (e.g., 108a) can function as a cathode type electrode and another one of the electrodes 108 (e.g., 108b) can function as an anode type electrode, or vice versa, when the electrodes are used for delivering stimulation. The electrode 108a is an example of a tip electrode, and the electrode 108b is an example or a ring electrode. The electrodes 108a and 108b can be referred to collectively as the electrodes 108, or individually as the electrode 108. While the LP 102 shown in FIG. 2 is shown as including only two electrodes 108, in alternative embodiments discussed below, an LP can include more than two electrodes. The LP 102 shown in FIG. 2 is also shown as including a retrieval feature 207, which can include a "button" or circular grasping feature that is configured to dock within a docking cap or a retrieval catheter that can be used to remove the LP 102 when it needs to be removed and/or replaced. Alternative form factors for the retrieval feature are also possible.

Where an LP includes more than two electrodes, a first subset of the electrodes can be used for delivering pacing pulses, a second subset of the electrodes can be used for sensing a near-field signal, a third subset of the electrodes can be used for sensing a far-field signal, and a fourth subset of the electrodes can be used for transmitting and receiving i2i messages. One or more of the first, second, third, and forth subsets of electrodes can be the same, or they can all differ from one another. As used herein, the term near-field signal refers to a signal that originates in a local chamber (i.e., the same chamber) within which or on which corresponding sense electrodes (and the LP including the sense electrodes) are located. Conversely, the term far-field signal refers to a signal that originates in a chamber other than the local chamber within which or on which corresponding sense electrodes (and the LP including the sense electrodes) are located.

The housing 202 can also include an electronics compartment 210 within the housing that contains the electronic components necessary for operation of the pacemaker, including, e.g., a pulse generator, receiver, and a processor for operation. The hermetic housing 202 can be adapted to be implanted on or in a human heart, and can be cylindrically shaped, rectangular, spherical, or any other appropriate shapes, for example.

The housing 202 can comprise a conductive, biocompatible, inert, and anodically safe material such as titanium, 316L stainless steel, or other similar materials. The housing 202 can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 2, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 2, the pacemaker can further include a header assembly 212 to isolate electrodes 108a and 108b. The header assembly 212 can be made from PEEK, tecothane or another biocompatible plastic, and can contain a ceramic to metal feedthrough, a glass to metal feedthrough, or other appropriate feedthrough insulator as known in the art.

The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 2, electrode 108a can be a pace/sense electrode and electrode 108b can be a return electrode. The electrode 108b can be a portion of the conductive housing 202 that does not include an insulator 208. As noted above, and described in additional detail below, an LP can include more than two electrodes, and may use different combinations of the electrodes for sensing a near-field signal, sensing a far-field signal, delivering pacing pulses, and sending and receiving i2i messages. When the electrode 108a is used as a pace electrode it can also be referred to as the cathode.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 2) into contact with stimulable tissue. Electrode 108b can serve as an indifferent electrode (also referred to as the anode) for sensing and pacing. The fixation mechanism may be coated partially or in full for electrical insulation, and a steroid-eluting matrix may be included on or near the device to minimize fibrotic reaction, as is known in conventional pacing electrode-leads.

Implant-to-Implant (i2i) Event Messaging

The LPs 102 can utilize implant-to-implant (i2i) communication through event messages to coordinate operation with one another in various manners. The terms i2i communication, i2i event messages, and i2i event markers are used interchangeably herein to refer to event related messages and IMD/IMD operation related messages transmitted from an implanted device and directed to another implanted device (although external devices, e.g., a programmer, may also receive i2i event messages). In certain embodiments, the LPs 102 operate as independent leadless pacers maintaining beat-to-beat multi-chamber functionality via a "Master/Slave" operational configuration. For descriptive purposes, the right atrial LP 102a can also be referred to as the "raLP", the right ventricular LP 102b can also be referred to as the "rvLP", and the left ventricular LP 102c can also be referred to as the "lvLP". One of the LPs 102a, 102b, and 102c can be designated as the "master" device, with the remaining LPs being "slave" devices. The master device, which can also be referred to as the master LP, orchestrates most or all decision-making and timing determinations (including, for example, rate-response changes). Since the master LP will perform more processing than the slave LPs, it would be beneficial of the master LP included a larger battery than the slave LPs, so that the longevity of the master LP is similar to the longevity of the slave LPs, Since the RV chamber has the most area available for implantation of an LP, the LP 102b that can be implanted in the LV chamber (i.e., the rvLP) is a good candidate for being the master LP, and for much of the remaining discussion it is assume that the LP 102b (i.e., the rvLP) is the master LP. However, in alternative embodiments, one of the other LPs, e.g., the LP 102a or the LP 102c the raLP or the lvLP) can be designated as the master. In accordance with certain embodiments, the LP 102 that is designated as the master device (e.g. rvLP) may implement all or most multi-chamber diagnostic and therapy determination algorithms.

In accordance with certain embodiments, methods are provided for coordinating operation between three LPs configured to be implanted entirely within (or alternatively on) first, second, and third chambers of the heart, namely the RA chamber, the RV chamber, and the LV chamber. A method transmits an event marker through conductive communication through electrodes located along a housing of the first LP, the event marker indicative of one of a local paced or sensed event. The method detects, over a sensing channel, the event marker at the second LP and/or the third LP. The method identifies the event marker at the second LP and/or the third LP based on a predetermined pattern configured to indicate that an event of interest has occurred in a remote chamber. In response to the identifying operation, the method initiates a related action in the second LP and/or the third LP. Additionally, the third LP can be responsive to an event caused or detected by the second LP.

Figure 3:
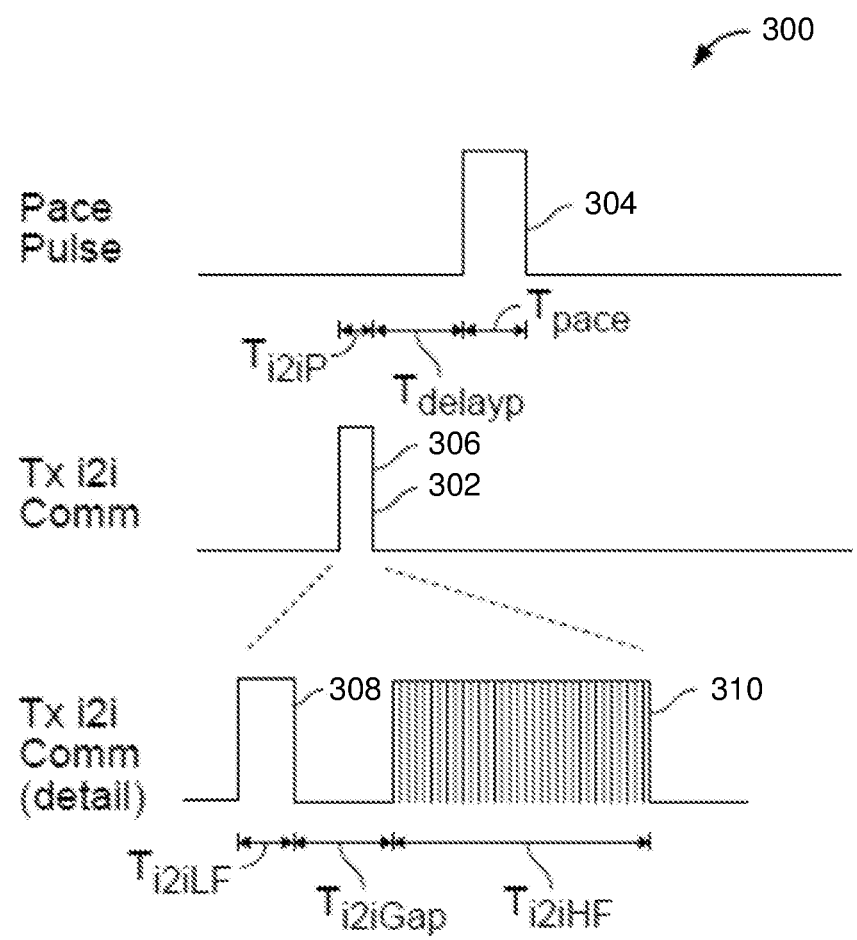
FIG. 3 is a timing diagram demonstrating one embodiment of implant to implant (i2i) communication for a paced event.

FIG. 3 is a timing diagram 300 demonstrating one example of an i2i communication for a paced event. The i2i communication may be transmitted, for example, from the LP 102a to the LP 102b and/or the LP 102c. As shown in FIG. 3, in this embodiment, an i2i transmission 302 is sent prior to delivery of a pace pulse 304 by the transmitting LP (e.g., LP 102). This enables the receiving LP (e.g., LP 102b) to prepare for the remote delivery of the pace pulse. The i2i transmission 302 includes an envelope 306 that may include one or more individual pulses. For example, in this embodiment, envelope 306 includes a low frequency pulse 308 followed by a high frequency pulse train 310. Low frequency pulse 308 lasts for a period $T_{i2iLF}$, and high frequency pulse train 310 lasts for a period $T_{i2iHF}$. The end of low frequency pulse 308 and the beginning of high frequency pulse train 310 are separated by a gap period, $T_{i2iGap}$.

As shown in FIG. 3, the i2i transmission 302 lasts for a period $T_{i2iP}$, and pace pulse 304 lasts for a period $T_{pace}$. The end of i2i transmission 302 and the beginning of pace pulse 304 are separated by a delay period, $T_{delayP}$. The delay period may be, for example, between approximately 0.0 and 10.0 milliseconds (ms), particularly between approximately 0.1 ms and 2.0 ms, and more particularly approximately 1.0 ms. The term approximately, as used herein, means +/−10% of a specified value.

Figure 4:
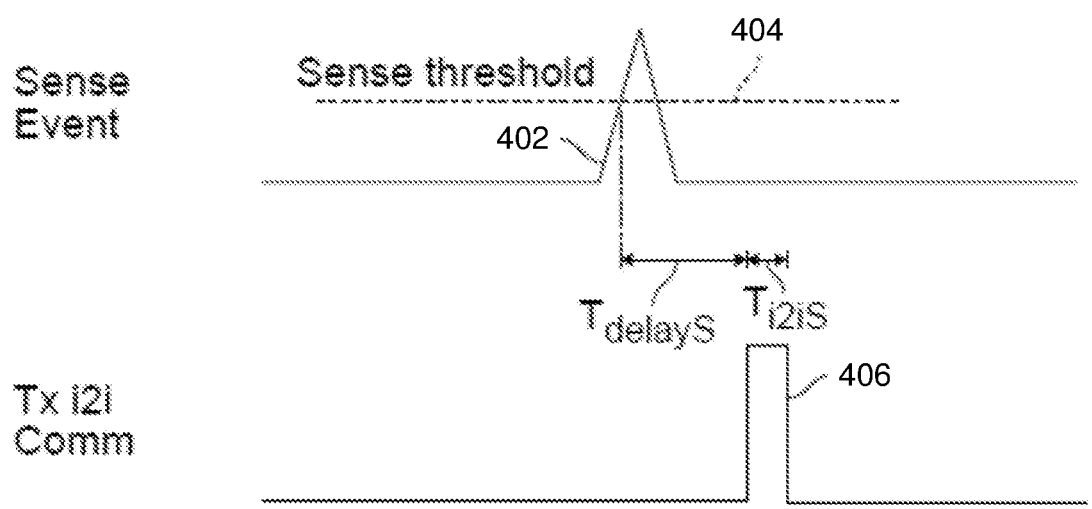
FIG. 4 is a timing diagram demonstrating one embodiment of i2i communication for a sensed event.

FIG. 4 is a timing diagram 400 demonstrating one example of an i2i communication for a sensed event. The i2i communication may be transmitted, for example, from the LP 102a to the LP 102b and/or the LP 102c. As shown in FIG. 4, in this embodiment, the transmitting LP (e.g., LP 102a) detects the sensed event when a sensed intrinsic activation 402 crosses a sense threshold 404. A predetermined delay period, $T_{delayS}$, after the detection, the transmitting LP transmits an i2i transmission 406 that lasts a predetermined period $T_{i2iS}$. The delay period may be, for example, between approximately 0.0 and 10.0 milliseconds (ms), particularly between approximately 0.1 ms and 2.0 ms, and more particularly approximately 1.0 ms.

As with i2i transmission 302, i2i transmission 406 may include an envelope that may include one or more individual pulses. For example, similar to envelope 306, the envelope of i2i transmission 406 may include a low frequency pulse followed by a high frequency pulse train.

Optionally, wherein the first LP is located in or on the RA chamber, the second LP is located in or on the RV chamber, and the third LP is located in or on the LV chamber, the first LP can produce an AS/AP event marker to indicate that an atrial sensed (AS) event or atrial paced (AP) event has occurred or will occur in the immediate future. For example, the AS and AP event markers may be transmitted following the corresponding AS or AP event. Alternatively, the first LP may transmit the AP event marker slightly prior to delivering an atrial pacing pulse. The second LP and/or the third LP can initiate an atrioventricular (AV) interval after receiving an AS or AP event marker from the first LP; and initiate a post atrial ventricular blanking (PAVB) interval after receiving an AP event marker from the first LP.

Optionally, the LPs may operate in a "pure" master/slave relation, where the master LP delivers "command" markers in addition to or in place of "event" markers. A command marker can direct one or more slave LPs to perform an action such as to deliver a pacing pulse and the like. For example, when a slave LP is located in an atrium and a master LP is located in a ventricle, in a pure master/slave relation, the slave LP delivers an immediate pacing pulse to the atrium when receiving an AP command marker from the master LP.

In accordance with some embodiments, communication and synchronization between the raLP, rvLP, and lvLP is implemented via conducted communication of markers/commands in the event messages (per i2i communication protocol). As explained above, conducted communication represents event messages transmitted from the sensing/pacing electrodes at frequencies outside the RF or Wi-Fi frequency range. Alternatively, the event messages may be conveyed over communication channels operating in the RF or Wi-Fi frequency range. The figures and corresponding description below illustrate non-limiting examples of markers that may be transmitted in event messages. The figures and corresponding description below also include the description of the markers and examples of results that occur in the LP that receives the event message. Table 2 represents exemplary event markers sent from the raLP to the rvLP and/or lvLP, while Table 3 represents exemplary event markers sent from the rvLP to the raLP and/or lvLP, or from the lvLP to the raLP and/or rvLP. In the master/slave configuration, AS event markers are sent from the aLP each time that an atrial event is sensed outside of the post ventricular atrial blanking (PVAB) interval or some other alternatively-defined atrial blanking period. The AP event markers are sent from the raLP each time that the raLP delivers a pacing pulse in the atrium. The raLP may restrict transmission of AS markers, whereby the raLP transmits AS event markers when atrial events are sensed both outside of the PVAB interval and outside the post ventricular atrial refractory period (PVARP) or some other alternatively-defined atrial refractory period. Alternatively, the raLP may not restrict transmission of AS event markers based on the PVARP, but instead transmit the AS event marker every time an atrial event is sensed.

TABLE 2

"A2V" Markers/Commands (e.g., from raLP to rvLP and/or lvLP)

| Marker | Description | Result in rvLP and/or lvLP |
|---|---|---|
| AS | Notification of a sensed event in atrium (if not in PVAB or PVARP) | Initiate AV interval (if not in PVAB or PVARP) |
| AP | Notification of a paced event in atrium | Initiate PAVB<br>Initiate AV interval (if not in PVARP) |

As shown in Table 2, when an raLP transmits an event message that includes an AS event marker (indicating that the raLP sensed an intrinsic atrial event), the rvLP and/or lvLP may initiate an AV interval timer. If the raLP transmits an AS event marker for all sensed events, then the rvLP and/or lvLP would preferably first determine that a PVAB or PVARP interval is not active before initiating an AV interval timer. If however the raLP transmits an AS event marker only when an intrinsic signal is sensed outside of a PVAB or PVARP interval, then the rvLP and/or lvLP could initiate the AV interval timer upon receiving an AS event marker without first checking the PVAB or PVARP status. When the raLP transmits an AP event marker (indicating that the raLP delivered or is about to deliver a pace pulse to the atrium), the rvLP and/or lvLP can initiate a PVAB timer and an AV interval time, provided that a PVARP interval is not active. The rvLP and/or lvLP may also blank its sense amplifiers to prevent possible crosstalk sensing of the remote pace pulse delivered by the raLP.

TABLE 3

"V2A" Markers/Commands (e.g., from rvLP, or lvLP, to raLP)

| Marker | Description | Result in raLP |
|---|---|---|
| VS | Notification of a sensed event in ventricle | Initiate PVARP |
| VP | Notification of a paced event in | Initiate PVAB |

TABLE 3-continued

"V2A" Markers/Commands (e.g., from rvLP, or lvLP, to raLP)

| Marker | Description | Result in raLP |
|---|---|---|
|  | ventricle | Initiate PVARP |
| AP | Command to deliver immediate pace pulse in atrium | Deliver immediate pace pulse to atrium |

As shown in Table 3, when the rvLP and/or lvLP senses a ventricular event, it can transmit an event message including a VS event marker, in response to which the raLP may initiate a PVARP interval timer. When the rvLP delivers or is about to deliver a pace pulse in the right ventricle, the rvLP transmits a VP event marker. When the raLP receives the VP event marker, the raLP can initiate a PVAB interval timer and also a PVARP interval timer. The raLP may also blank its sense amplifiers to prevent possible crosstalk sensing of the remote pace pulse delivered by the rvLP. The rvLP may also transmit an event message containing an AP command marker to command the raLP to deliver an immediate pacing pulse in the atrium upon receipt of the command without delay.

The foregoing event markers are examples of a subset of markers that may be used to enable the raLP, rvLP and lvLP to maintain full CRT functionality. In one embodiment, the master LP (e.g., the rvLP) may perform all CRT algorithms, while the raLP may perform atrial-based hardware-related functions, such as PVAB, implemented locally within the raLP. In this embodiment, the raLP is effectively treated as a remote 'wireless' atrial pace/sense electrode. In another embodiment, the master LP (e.g., the rvLP) may perform most but not all CRT algorithms, while the raLP may perform a subset of diagnostic and therapeutic algorithms. In an alternative embodiment, rvLP, lvLP and raLP may equally perform diagnostic and therapeutic algorithms. In certain embodiments, decision responsibilities may be partitioned separately to one of the raLP, rvLP or lvLP. In other embodiments, decision responsibilities may involve joint inputs and responsibilities.

In the event that LP to LP (i2i) communication is lost (prolonged or transient), the system 100 may automatically revert to safe ventricular-based pace/sense functionalities as the rvLP device is running all of the necessary algorithms to independently achieve these functionalities. For example, if the rvLP loses i2i communication it may revert from the VDD mode to a VVI mode or a VDI mode, and if the raLP loses i2i communication it may revert from ADD mode to an OAO mode or an AAI mode. Thereafter, once i2i communication is restored, the system 100 can automatically resume CRT functionalities.

As also noted above, a transmitter (e.g., 118) of an LP 102 may be configured to transmit event messages in a manner that does not inadvertently capture the heart in the chamber where LP 102 is located, such as when the associated chamber is not in a refractory state. In addition, an LP 102 that receives an event message may enter an "event refractory" state (or event blanking state) following receipt of the event message. The event refractory/blanking state may be set to extend for a determined period of time after receipt of an event message in order to avoid the receiving LP 102 from inadvertently sensing another signal as an event message that might otherwise cause retriggering. For example, the receiving LP 102 may detect a measurement pulse from another LP 102. The amplitude of a detected (i.e., sensed) measurement pulse can be referred to as the sensed amplitude.

Referring back to FIG. 2, the LP 102 shown therein included just two electrodes, including the tip electrode 108a and the ring electrode 108b. As noted above, one or more of the LPs 102 can include more than two electrodes. Examples of LPs 102 that include three electrodes are described below with reference to FIGS. 5A and 5B.

Leadless Pacemaker (LP) Implementations

Figure 5A:
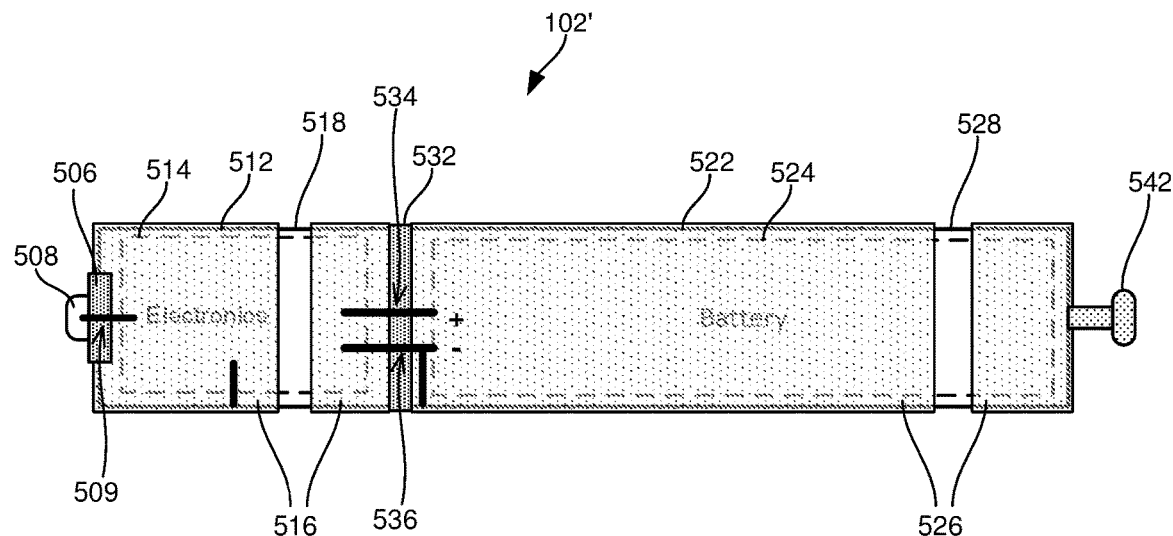
FIGS. 5A and 5B illustrate exemplary LPs that enables the LPs to effectively deliver pacing pulses to the cardiac chamber within or on which the LP is implanted, effectively sense near-field signals, as well as effectively sense far-field signals.
Figure 5B:
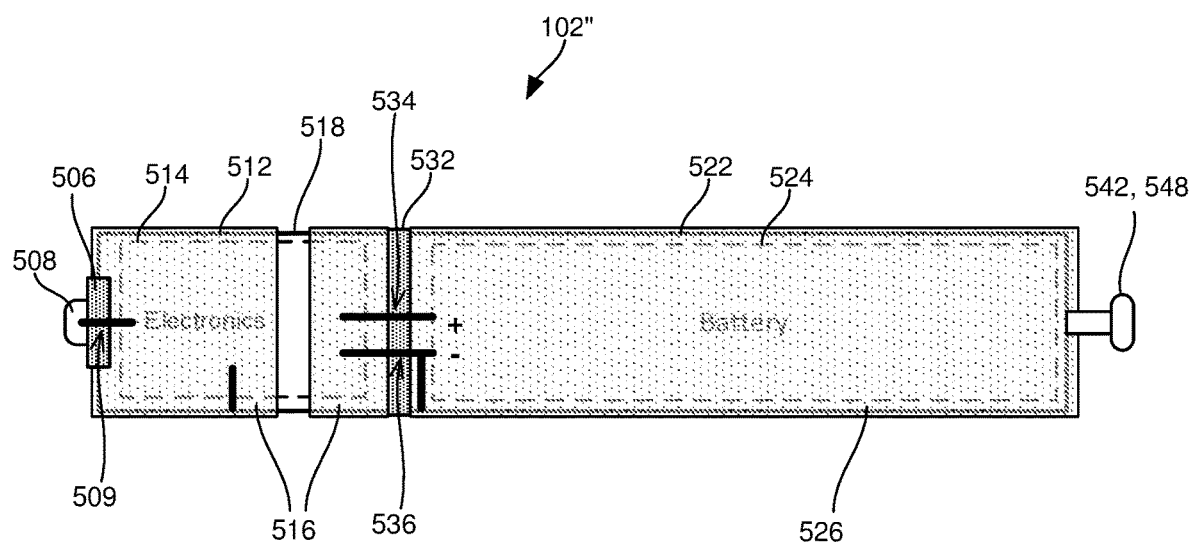

FIGS. 5A and 5B illustrate exemplary LPs that enables the LPs to effectively deliver pacing pulses to the cardiac chamber within or on which the LP is implanted, effectively sense near-field signals, as well as effectively sense far-field signals. A near-field signal can be used by the LP that senses the near-field signal to monitor electrical cardiac activity of the cardiac chamber within or on which the LP is implanted, which cardiac chamber can be referred to as the local chamber. A far-field signal can be used by the LP that senses the far-field signal to monitor electrical cardiac activity associated with another chamber of the heart (within or on which the LP that obtains the far-field signal is not implanted). Such other cardiac chamber of the heart (within or on which an LP is not implanted) can also be referred to herein as a remote chamber. The LP can also perform i2i communications.

Referring to FIG. 5A, an LP 102', according to an embodiment of the present technology, is shown therein. The LP 102' is shown as including two separate housings 512 and 522, each of which is made of an electrically conductive material. The housings 512 and 522 can be made of the same type of electrically conductive material as one another, or of different types of electrically conductive materials than one another. The electrically conductive material of which the housing 512 and/or the housing 522 is made can be an electrically conductive biocompatible metal or alloy, such as stainless steel, a cobalt-chromium alloy, titanium, or a titanium alloy, but is not limited thereto. It would also be possible for the electrically conductive material of which the housing 512 and/or the housing 522 is made to be a currently developed or future developed electrically conductive polymeric material. Since the housings 512 and 522 are each made of an electrically conductive material, they can also be referred to as electrically conductive housings 512 and 522.

As shown in FIG. 5A, electronic circuitry 514 (also referred to as electronics) is included within the housing 512, and a battery 524 (e.g., the battery 114 in FIG. 1B) is located within the housing 522. The electronic circuitry 512 can include, e.g., one or more pulse generators, one or more sense amplifiers, switches, a controller, memory, and/or the like. Such a controller can include one or more processors, and/or an application-specific integrated circuit (ASIC), but is not limited thereto. Exemplary details of the electronic circuitry 512 were discussed above with reference to FIG. 1B, and are also discussed below with reference to FIG. 11. Since the electronic circuitry 512 can likely be made smaller in size that the battery 524 (which should preferably power the LP for a few years), it is likely that the housing 522 which encases the battery 524 is larger in volume than the housing 512 which encases the electronic circuitry 514. The housings 512 and 522 are preferably hermetic housings that protect the electronic circuitry 514 and the battery 524 from the harsh environment of the human body.

Still referring to FIG. 5A, an inter-housing insulator 532 is located between the housing 512 and the housing 522 to electrically isolate the housings 512 and 514 from one another. The inter-housing insulator 532 can be made, e.g., of sapphire, ruby, a biocompatible glass (e.g., borosilicate glass) or a biocompatible ceramic, but is not limited thereto. Exemplary biocompatible ceramics include, but is not limited aluminum nitride (AlN), zirconia (ZrO2), silicon carbide (SiC), and silicon nitride (Si3N4).

In certain embodiments each of the housings 512 and 522 has a generally cylindrical shape. As shown in FIG. 5A, each of the housings 512 and 522 has an end that is connected to the inter-housing insulator 532, and an opposing end that can be referred to as the "free end" of the respective housing. The end of each housing 512 and 522 that is not the free end can be referred to as the "non-free end". The non-free end of the housing 512 can be physically attached to a first side of the inter-housing insulator 532. Similarly, the non-free end of the housing 522 can be physically attached to a second side of the inter-housing insulator 532. Where each of the housings 512 and 522 has a generally cylindrical shape the inter-housing insulator may have an annular shape or a disk-like shape, but is not limited thereto. For more specific examples, the inter-housing insulator 532 can be an annular shaped ceramic or glass collar.

Preferably there is a hermetic bonding between the non-free end of the housing 512 and the first side of the inter-housing insulator 532, and a hermetic bonding between the non-free end of the housing 522 and the second side of the inter-housing insulator 532. For example, fusion welding methods, such as laser welding, tungsten inert gas welding (TIG), or electron-beam welding can be used to hermetically bond ends of each of the first and second housings 512 and 522 to the first and second sides of the inter-housing insulator 532. In certain embodiments, multiple hermetic seals are provided between an end of a housing (512 or 522) and a side of the inter-housing insulator. Such hermetic seals can include, e.g., one or more glass-to-tantalum seals produced by melting glass with an infrared laser beam, and one or more hermetic seals obtained by melting a tantalum tube closed in a plasma needle arc welder, but are not limited thereto.

The battery 524 can be any one of various different types of batteries, such as, but not limited to, a lithium battery, e.g., a lithium carbon monofluoride (Li—CFx) battery. The use of other types of batteries is also possible and within the scope of the embodiments described herein. The battery 524 has a positive (+) pole and a negative (−) pole. In accordance with certain embodiments where the battery 524 is an Li—CFx battery, lithium (Li) provides the anode or negative (−) pole of the battery, and carbon monofluoride (CFx) provides the cathode or positive (+) pole of the battery. When referring to the battery 524, the positive (+) pole can also be referred to as the positive (+) terminal, and the negative (−) pole can also be referred to as the negative (−) terminal.

In accordance with certain embodiments, the negative (−) pole of the battery 524 is connected to the electrically conductive housing 522 that encases the battery 524. The connection between the negative (−) pole of the battery 524 and the electrically conductive housing 522 can be via a wire or other electrical conductor. Alternatively, the battery 524 can be designed and manufactured such that the outer-casing of the battery 524 is electrically connected to the negative (−) pole of the battery, or more generally, provides the negative (−) pole for the battery. Where the outer-casing of the battery 524 provides the negative (−) pole of the battery, then the negative (−) pole of the battery 524 will be connected to the electrically conductive housing 522 so long as the outer-casing of the battery 524 is physically in contact with the electrically conductive housing 522. Unless stated otherwise, it will be assumed that the outer-casing of the battery 524 provides the negative (−) pole of the battery. However, it should be noted that in alternative embodiments the battery 524 can be designed and manufactured such that the outer-casing of the battery 524 is electrically connected to the positive (+) pole of the battery, or more generally, provides the positive (+) pole for the battery.

Conductors 534 and 536 that extend through the inter-housing insulator 532 connect the positive (+) and negative (−) poles of the battery 524 to the electronics 514, which are encased within the electrically conductive housing 512, to thereby enable the battery 524 to provide power to the electronics 514.

The LP 102' is shown as including a tip electrode 508 that is located adjacent to the free end of the housing 512. The tip electrode 508 is electrically isolated from the electrically conductive housing 512 by an insulator 506. A feedthrough 509 that extends through the insulator 506 is used to connect the tip electrode 508 to the electronics 514 (e.g., one or more pulse generators and/or one or more sense amplifiers). The tip electrode 508 can have various different shapes, depending upon implementation. For example, the tip electrode 508 can have an annular shape, a semi-spherical cap, or a helical shape to enable the tip electrode 508 to also function as an attachment mechanism for attaching the LP 102' to an interior or exterior wall of a cardiac chamber. Where the tip electrode 508 has a helical shape it can also be referred to as a helical or helix electrode. Other shapes for the tip electrode 508 are also possible and within the embodiments of the present technology described herein.

The LP 102' is also shown as including a ring electrode 518 and a ring electrode 528. In certain embodiments, the ring electrode 518 is provided by a non-insulated portion of the electrically conductive housing 512. More specifically, portions of the electrically conductive housing 512 can be coated or otherwise covered by an insulator 516, and a non-insulated portion of the housing 512 can provide the ring electrode 518. Similarly, the ring electrode 528 can be provided by a non-insulated portion of the electrically conductive housing 522. More specifically, portions of the electrically conductive housing 522 can be coated or otherwise covered by an insulator 526, and a non-insulated portion of the housing 522 can provide the ring electrode 528. Such insulators 516 and 526 can be made various different types of biocompatible insulating materials, such as, but not limited to, ceramic, polyurethane, parylene, or silicone.

Where the outer-casing of the battery 524 provides the negative (−) pole of the battery, and the outer-casing of the battery 524 is physically in contact with the electrically conductive housing 522, then the electrically conductive housing 522 is electrically connected to the negative (−) pole (aka the negative terminal) of the battery 524. When using such a battery 524, an advantage of having the inter-housing insulator 532 electrically isolate the housings 512 and 522 from one another is that a single common feedthrough (536 in FIG. 5A) can be used to connect the electronics 514 to the negative (−) pole of the battery 524 and the ring electrode 528. A further advantage of having the inter-housing insulator 532 electrically isolate the housings 512 and 522 from one another is that a non-insulated portion of each of the housings can be used to provide respective ring electrodes 518 and 528. Another advantage of having the inter-housing insulator 532 electrically isolate the housings 512 and 522 from one another is that the ring electrodes 518 and 528 can be used independently of one another. Further, it is noted that designing an LP to include three electrodes should enable better sensing of far-field signals, compared to if the LP included only two electrodes.

In accordance with certain embodiments, during pacing of a cardiac chamber (e.g., RA chamber, RV chamber, or LV chamber) within or on which the LP 102' is implanted, the tip electrode 508 is connected as the cathode and one of the ring electrodes 518 or 528 is connected as the anode. In other words, a tip-to-ring pacing vector can be used for pacing. It would also be possible that when performing pacing using the tip electrode 508 as the cathode, both ring electrodes 518 and 528 can be connected as the anode (e.g., a distributed anode) at the same time. In accordance with certain embodiments, sensing can be performed using one or more pair of the electrodes 508, 518, and 528. Additionally, i2i communication can be performed using a pair of the electrodes 508, 518, and 528.

In an embodiment, if the LP 102' is implanted within the RV chamber, then near-field sensing (of electrical cardiac activity associated with the RV chamber) can be performed using the tip electrode 508 and the ring electrode 518. In other words, a tip-to-ring sensing vector can be used for near-field sensing. In an embodiment, if the LP 102' is implanted in the RV chamber, then far-field sensing (of electrical cardiac activity associated with the RA chamber) can be performed using the tip electrode 508 and the ring electrode 528, since the ring electrode 528 will be the electrode closest to the RA chamber. In other words, a separate tip-to-ring sensing vector can be used for far-field sensing than is used for near-field sensing. In still another embodiment, if the LP 102' is implanted in the RV chamber, far-field sensing (of electrical cardiac activity associated with the RA chamber) can be performed using the ring electrode 518 and the ring electrode 528. In other words, a ring-to-ring sensing vector can be used for far-field sensing. The tip electrode 508 and the ring electrode 528 can be used for i2i communication (both transmitting of i2i pulses and receiving of i2i pulses) with another LP, another ND, and/or with an external device (e.g., programmer). Alternatively, the tip electrode 508 and the ring electrode 518 can be used for i2i communication (both transmitting of i2i pulses and receiving of i2i pulses) with another LP, another IMD, and/or with an external device. In still other embodiments, the ring electrode 518 and the ring electrode 528 can be used for i2i communication (both transmitting of i2i pulses and receiving of i2i pulses) with another LP, another IMD, and/or with an external device.

In an embodiment, if the LP 102' is implanted within the RA chamber, then near-field sensing (of electrical cardiac activity associated with the RA chamber) can be performed using the tip electrode 508 and the ring electrode 518 (i.e., a tip-to-ring sensing vector can be used for near-field sensing); far-field sensing (of electrical cardiac activity associated with the RV chamber) can be performed using the tip electrode 508 and the ring electrode 528 (since the ring electrode 528 will be the electrode closest to the RV chamber) or using the ring electrode 518 and the ring electrode 528; and the tip electrode 508 and one of the ring electrodes 518 or 528 can be used for i2i communication (both transmitting of i2i pulses and receiving of i2i pulses) with another LP, another IMD, and/or with an external device, or the two ring electrode 518 and 528 can be used for i2i communication.

More generally, when the LP 102' is implanted within a cardiac chamber, near-field sensing (of electrical cardiac activity associated with the local chamber within which the LP 102' is implanted) can be performed using the tip electrode 508 and the ring electrode 518 (i.e., a tip-to-ring sensing vector can be used for near-field sensing); far-field sensing (of electrical cardiac activity associated with a remote chamber) can be performed using the tip electrode 508 and the ring electrode 528, or using the ring electrode 518 and the ring electrode 528; and i2i communication can be performed using the tip electrode 508 and one of the ring electrodes 518 or 528, or using both ring electrode 518 and 528. Other variations are also possible and within the scope of the embodiments of the present technology.

Still referring to FIG. 5A, the LP 102' is also shown as including a retrieval feature 542, which can include a "button" or circular grasping feature that is configured to dock within a docking cap or a retrieval catheter that can be used to remove the LP 102' when it needs to be removed and/or replaced. Alternative form factors for the retrieval feature are also possible. The retrieval feature 542 can be made of a non-electrically conductive material, i.e., an insulating material. Alternatively, the retrieval feature 542 can be made of an electrically conductive material, and in the embodiment of FIG. 5A, can be coated or otherwise covered by a biocompatible insulating materials, such as, but not limited to, ceramic, polyurethane, parylene, or silicone.

FIG. 5B is an illustration of a leadless pacemaker (LP) 102" according to another embodiment of the present technology. Elements in FIG. 5B that are the same or similar to elements in FIG. 5A are numbered the same and need not be described again in the same amount of detail. In accordance with certain embodiments, the retrieval feature 542 (or at least a portion thereof) is made of an electrically conductive material and is electrically connected to the negative (−) pole of the battery 524. This enables the retrieval feature 542 (or at least a portion thereof) to be another tip electrode 548. Accordingly, the LP 102" includes the tip electrode 508 adjacent to the free end of the housing 512, as well as a tip electrode adjacent to the free end of the housing 522. Where the retrieval feature 542 provides a tip electrode 548, it can also be referred to as the tip electrode 542/548. A comparison between FIGS. 5A and 5B shows that a distinction of the LP 102" is that instead of having one tip electrode and two ring electrodes, as was the case with the LP 102', the LP 102" has two tip electrodes and one ring electrode. It would also be possible that a portion of the free end of the housing 522 is not coated or otherwise covered with an insulated material to thereby provide a tip electrode adjacent to the free end of the housing 522. This would also provide the LP 102" with two tip electrodes and one ring electrode.

In accordance with certain embodiments, during pacing of a cardiac chamber (e.g., RA chamber, RV chamber, or LV chamber) within or on which the LP 102" is implanted, the tip electrode 508 is connected as the cathode and the ring electrodes 518 is connected as the anode. In other words, a tip-to-ring pacing vector can be used for pacing. In accordance with certain embodiments, sensing can be performed using one or more pair of the electrodes 502, 518, and 548. Additionally, i2i communication can be performed using a pair of the electrodes 502, 518, and 548.

In an embodiment, if the LP 102" is implanted within the RV chamber, then near-field sensing (of electrical cardiac activity associated with the RV chamber) can be performed using the tip electrode 508 and the ring electrode 518. In other words, a tip-to-ring sensing vector can be used for near-field sensing. In an embodiment, if the LP 102" is implanted in the RV chamber, then far-field sensing (e.g., of electrical cardiac activity associated with the RA chamber) can be performed using the tip electrode 508 and the tip electrode 548, since the tip electrode 548 will be the electrode closest to the RA chamber. In other words, a tip-to-tip sensing vector can be used for far-field sensing. In still another embodiment, if the LP 102" is implanted in the RV chamber, far-field sensing (e.g., of electrical cardiac activity associated with the RA chamber) can be performed using the ring electrode 518 and the tip electrode 548. In other words, a ring-to-tip sensing vector can be used for far-field sensing. The tip electrode 508 and the tip electrode 548 can be used for i2i communication (both transmitting of i2i pulses and receiving of i2i pulses) with another LP, another IMD, and/or for implant to programmer (i2p) communication with an external device. Alternatively, the ring electrode 518 and the tip electrode 548 can be used for i2i communication (both transmitting of i2i pulses and receiving of i2i pulses) with another LP, another IMD, and/or for i2p communication with an external device.

In an embodiment, if the LP 102" is implanted within the RA chamber, then near-field sensing (e.g., of electrical cardiac activity associated with the RA chamber) can be performed using the tip electrode 508 and the ring electrode 518 a tip-to-ring sensing vector can be used for near-field sensing); far-field sensing (e.g., of electrical cardiac activity associated with the RV chamber) can be performed using the tip electrode 508 and the tip electrode 548 (since the tip electrode 548 will be the electrode closest to the RV chamber) or using the ring electrode 518 and the tip electrode 548. The tip electrode 508 and the tip electrode 548, or the ring electrode 518 and the tip electrode 548, can be used for i2i communication (both transmitting of i2i pulses and receiving of i2i pulses) with another LP, another IMD, and/or for i2p communication with an external device.

More generally, when the LP 102" is implanted within a cardiac chamber, near-field sensing (of electrical cardiac activity associated with the local chamber within which the LP 102" is implanted) can be performed using the tip electrode 508 and the ring electrode 518 (i.e., a tip-to-ring sensing vector can be used for near-field sensing); far-field sensing (of electrical cardiac activity associated with a remote chamber) can be performed using the tip electrode 508 and the tip electrode 548, or using the ring electrode 518 and the tip electrode 548; and i2i communication can be performed using the tip electrode 508 and the tip electrode 548, or using the ring electrode 518 and the tip electrode 548. Other variations are also possible and within the scope of the embodiments of the present technology.

Referring briefly back to FIG. 1B, only one sense amplifier 132 was shown within the LP illustrated therein. In accordance with certain embodiments, an LP (e.g., 102, 102' or 102") includes multiple sense amplifier, e.g., one or more for sensing near-field signals, one or more for sensing far-field signals, and one or more for sensing i2i signals. In FIG. 1B only one pulse generator 116 was shown within the LP illustrated therein. In accordance with certain embodiments, an LP (e.g., 102, 102' or 102") includes multiple pulse generators, e.g., one for generating pacing signals, and one or more for generating i2i signals. Further, it should be noted that where an LP (e.g., 102, 102' or 102") includes three or more electrodes, switch circuitry can be located between the electrodes and the sense amplifier(s) and pulse generator(s), to enable a controller to control which electrodes are used to sense a near-field signal, which electrodes are used to sense a far-field signal, which electrodes are used for pacing, and to control which electrodes are used for i2i communications.

Use of Far-Field and/or Sensor Signals to Supplement or Replace i2i Messaging

In accordance with certain embodiments of the present technology, one or more accelerometers of an LP can be used to determine when the LP is likely in a deaf zone, and during such periods the LP can rely on far-field sensing to time delivery of pacing within the chamber in which the LP is implanted. For example, the raLP can sense a far-field signal from which electrical cardiac activity associated with the RV chamber can be detected, and the raLP can perform ADD pacing by timing delivery of atrial pulses based on the timing of cardiac activity associated with the RV chamber as detected from the far-field signal. For another example, the rvLP can sense a far-field signal from which electrical cardiac activity associated with the RA chamber can be detected, and the rvLP can perform VDD pacing by timing delivery of ventricular pulses based on the timing of cardiac activity associated with the RA chamber as detected from the far-field signal. When an raLP implanted in the RA chamber times delivery of atrial pacing pulses based on the timing of RV cardiac activity as detected from a far-field signal sensed by the raLP, it can be said that the raLP times its delivery of atrial pacing pulses based on timing of RV cardiac activity detected by the raLP itself. Similarly, when an rvLP implanted in the RV chamber times delivery of ventricular pacing pulses based on the timing of RA cardiac activity as detected from a far-field signal sensed by the rvLP, it can be said that the rvLP times its delivery of ventricular pacing pulses based on timing of RA cardiac activity as detected by the rvLP itself.

Depending upon the specific implementation, an raLP can primarily or by default time delivery of RA pacing pulses based on the timing of cardiac activity associated with the RV chamber as determined based on i2i messages received by the raLP from a rvLP, and the raLP can, as a backup, time delivery of RA pacing pulses based on the timing of cardiac activity associated with the RV chamber that the raLP detected itself from a far-field signal that the aLP sensed. Similarly, a rvLP can primarily or by default time delivery of RV pacing pulses based on the timing of cardiac activity associated with the RA chamber as determined based on i2i messages received by the rvLP from an raLP, and the rvLP can, as a backup, time delivery of RV pacing pulses based on the timing of cardiac activity associated with the RA chamber that the rvLP detected itself from a far-field signal that the rvLP sensed.

Alternatively, an raLP can primarily or by default time delivery of RA pacing pulses based on the timing of cardiac activity associated with the RV chamber as determined based on a far-field signal that the raLP sensed itself, and the raLP can, as a backup, time delivery of RA pacing pulses based on the timing of cardiac activity associated with the RV chamber as determined based on i2i messages received by the raLP from a rvLP. Similarly, a rvLP can primarily or by default time delivery of RV pacing pulses based on the timing of cardiac activity associated with the RA chamber as determined based on a far-field signal that the rvLP sensed itself, and the rvLP can, as a backup, time delivery of RV pacing pulses based on the timing of cardiac activity associated with the RA chamber as determined based on i2i messages received by the rvLP from an raLP.

In accordance with certain embodiments of the present technology, instead of (or in addition to) an LP detecting electrical cardiac activity associated with another chamber based on a far-field signal sensed by the LP itself, the LP can use a sensor (e.g., an accelerometer or pressure sensor) to produce a sensor signal from which mechanical cardiac activity associated with another chamber of the heart may be detected. For example, the raLP can use an accelerometer or pressure sensor to produce a sensor signal from which heart sounds associated with the RV chamber can be detected, and the raLP can perform ADD pacing by timing delivery of atrial pulses based on the timing of cardiac activity associated with the RV chamber as detected from the sensor signal. For another example, the rvLP can use an accelerometer or pressure sensor to produce a sensor signal from which mechanical cardiac activity associated with the RA chamber can be detected, and the rvLP can perform VDD pacing by timing delivery of ventricular pulses based on the timing of cardiac activity associated with the RA chamber as detected from the sensor signal.

Where the rvLP performs VDD pacing, it performs ventricular pacing, atrial and ventricular (i.e., dual) sensing, dual (i.e., triggered and inhibited) response to a sensed event. VDD may be used, e.g., for AV nodal dysfunction but intact and appropriate sinus node behavior. The ventricular sensing can be based on a near-field signal that the rvLP senses itself using a pair of its electrodes. Similarly, if the rvLP performs VVI or VDI pacing, it can perform ventricular sensing based on a near-field signal that the rvLP senses itself using a pair of its electrodes. Atrial sensing can be based on a far-field signal that the rvLP senses itself using a pair of its electrodes, based on a sensor signal that rvLP senses itself (e.g., using an accelerometer or pressure sensor of the rvLP), and/or based on i2i messages that the vLP receives from the aLP.

Where the raLP performed ADD pacing, it performs atrial pacing, atrial and ventricular (i.e., dual) sensing, dual (i.e., triggered and inhibited) response to a sensed event. The atrial sensing can be based on a near-field signal that the raLP senses itself using a pair of its electrodes. Similarly, if the raLP performs AAI or ADI pacing, it can perform atrial sensing based on a near-field signal that the raLP senses itself using a pair of its electrodes. Ventricular sensing can be based on a far-field signal that the raLP senses itself using a pair of its electrodes, based on a sensor signal that raLP senses itself (e.g., using an accelerometer or pressure sensor of the raLP), and/or based on i2i messages that the raLP receives from the rvLP.

Any LP, of the raLP, the rvLP, and the lvLP, can deliver its pacing pulses based on timing it determines itself, e.g., from a far-field signal or a sensor signal the LP senses itself, or it can deliver its pacing pulses based on timing determined from i2i signals received by the LP from one or more other LPs. Far-field sensing that is performed by the raLP (e.g., 102a) is of electrical activity in the ventricles. Far-field sensing that is performed by the rvLP (e.g., 102b) is of electrical activity in the atrium and/or LV. Far-field sensing that is performed by the lvLP (e.g., 102c) is of electrical activity in the atrium and/or RV.

Cardiac Resynchronization Therapy (CRT)

Figure 6:
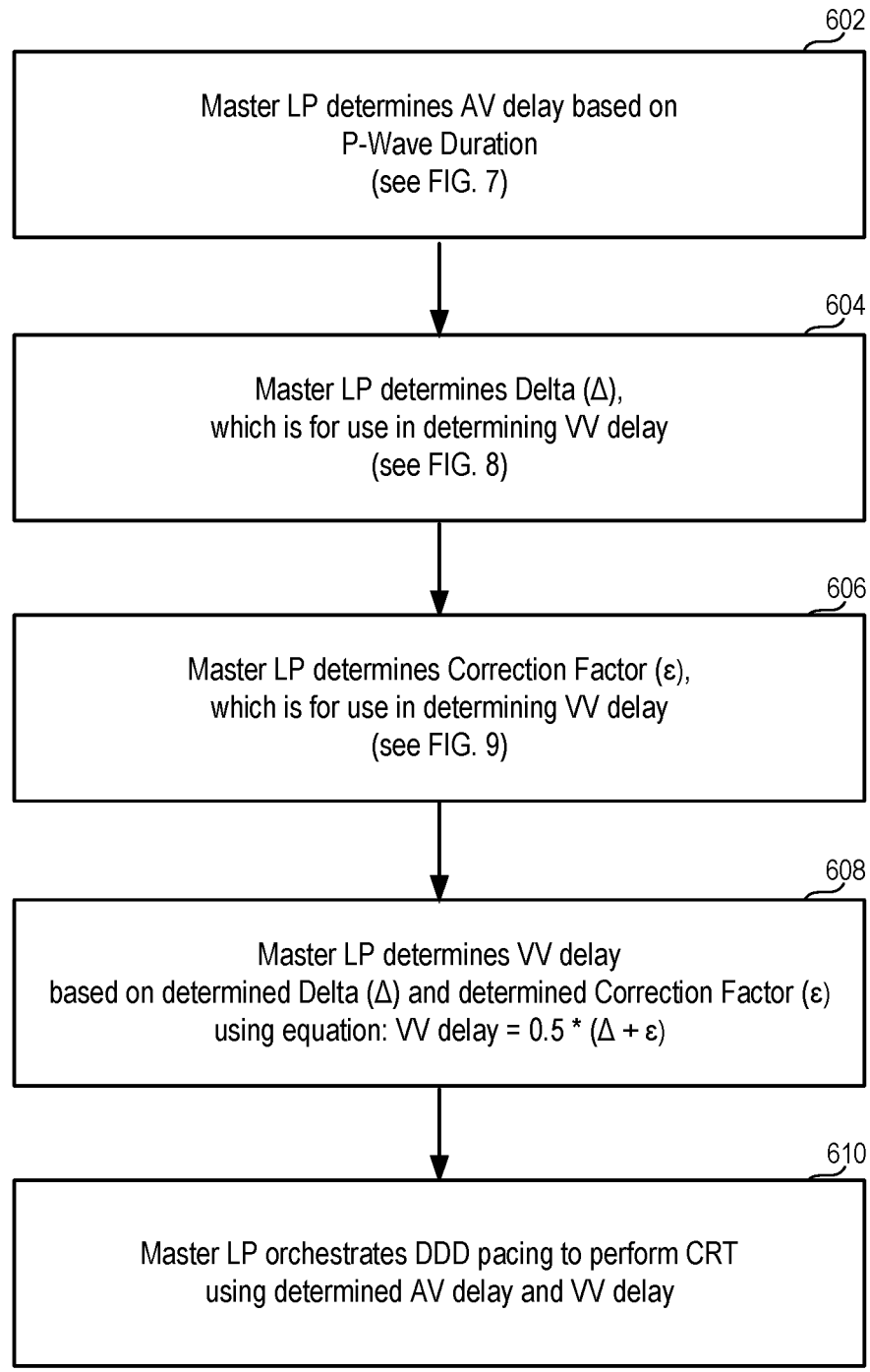
FIG. 6 is a high level flow diagram that is used to describe certain embodiments of the present technology for performing cardiac resynchronization therapy (CRT) using an implantable leadless pacemaker system including an LP implanted in or on the RA chamber, an LP implanted in or on the RV chamber, and an LP implanted in or on the LV chamber, wherein one of the LPs is designated a master LP.

The high level flow diagram of FIG. 6 will now be used to describe certain embodiments of the present technology for performing cardiac resynchronization therapy (CRT) using an implantable leadless pacemaker system including an LP implanted in or on the RA chamber, an LP implanted in or on the RV chamber, and an LP implanted in or on the LV chamber, wherein one of the LPs is designated a master LP. As noted above, the LP implanted in or on the RA chamber can also be referred to as the raLP, the LP implanted in or on the RV chamber can also be referred to as the rvLP, and the LP implanted in or on the LV chamber can also be referred to as the lvLP. Referring briefly back to FIG. 1A, the LP 102a is an example of the raLP, the LP 102b is an example of the rvLP, and the LP 102c is an example of the lvLP. FIGS. 1B and 2 illustrate exemplary implementation details of the LPs 102, according to certain embodiments of the present technology. The LPs can instead be implemented in accordance with the embodiments described with reference to FIG. 5A or 5B, but are not limited thereto.

As noted above, one of the raLP, rvLP, and lvLP is designated the master LP. The other two LPs, which are not designated the master LP, are considered slave LPs. Since the master LP will perform more processing than the slave LPs, it would be beneficial of the master LP included a larger battery than the slave LPs, so that the longevity of the master LP is similar to the longevity of the slave LPs, as was also noted above. Since the RV chamber has the most area available for implantation of an LP, the rvLP is a good candidate for being the master LP, and for the discussion of the flow diagram in FIG. 6 it will be assumed that the rvLP is the master LP. However, in alternative embodiments, the raLP or the lvLP can instead be designated as the master. The steps described with reference to FIGS. 6-10 can be performed solely by the LPs under the supervision of the LP that is designed the master LP. Alternatively, an external programmer that wirelessly communications with the LPs can supervise and/or assist with at least some of the steps.

Referring to FIG. 6, step 602 involves the master LP (e.g., the rvLP) determining an AV delay (to use for CRT) based on a P-wave duration. Additionally details of step 602, according to an embodiment of the technology, are described below with reference to FIGS. 7A, 7B and 7C, which can be collectively referred to as FIG. 7.

Still referring to FIG. 6, step 604 involves the master LP (e.g., the rvLP) determining a value for a variable "delta" ($\Delta$) that is for use in determining a VV delay (to use for CRT). The variable "delta" ($\Delta$) represents an interventricular delay that is based an atrio-ventricular delay for the LV chamber and an atrio-ventricular delay for the RV chamber. Additionally details of step 604, according to an embodiment of the technology, are described below with reference to FIG. 8.

Still referring to FIG. 6, step 606 involves the master LP (e.g., the rvLP) determining a value for a variable epsilon ($\epsilon$) (also known as a "correction factor") that is also for use in determining the VV delay (to use for CRT). Additionally details of step 606, according to an embodiment of the technology, are described below with reference to FIG. 9.

Still referring to FIG. 6, step 608 involves the master LP (e.g., the rvLP) determining the VV delay (to use for CRT) based on the determined values for the delta ($\Delta$) and the correction factor ($\epsilon$), that were determined at steps 604 and 606, respectively. In accordance with specific embodiments, the equation used to determine the VV delay at step 608 is as follows:

$$VV\ \text{delay} = 0.5 * (\Delta + \epsilon).$$

Finally, at step 610, the master LP (e.g., the rvLP) orchestrates DOD pacing, to perform CRT, using the AV delay and the VV delay, determined at steps 602 and 608, respectively. Additional details of step 610, according to certain embodiments of the present technology, are described below, following the discussion of FIGS. 7-9, e.g., with reference to FIG. 10.

Figure 8:
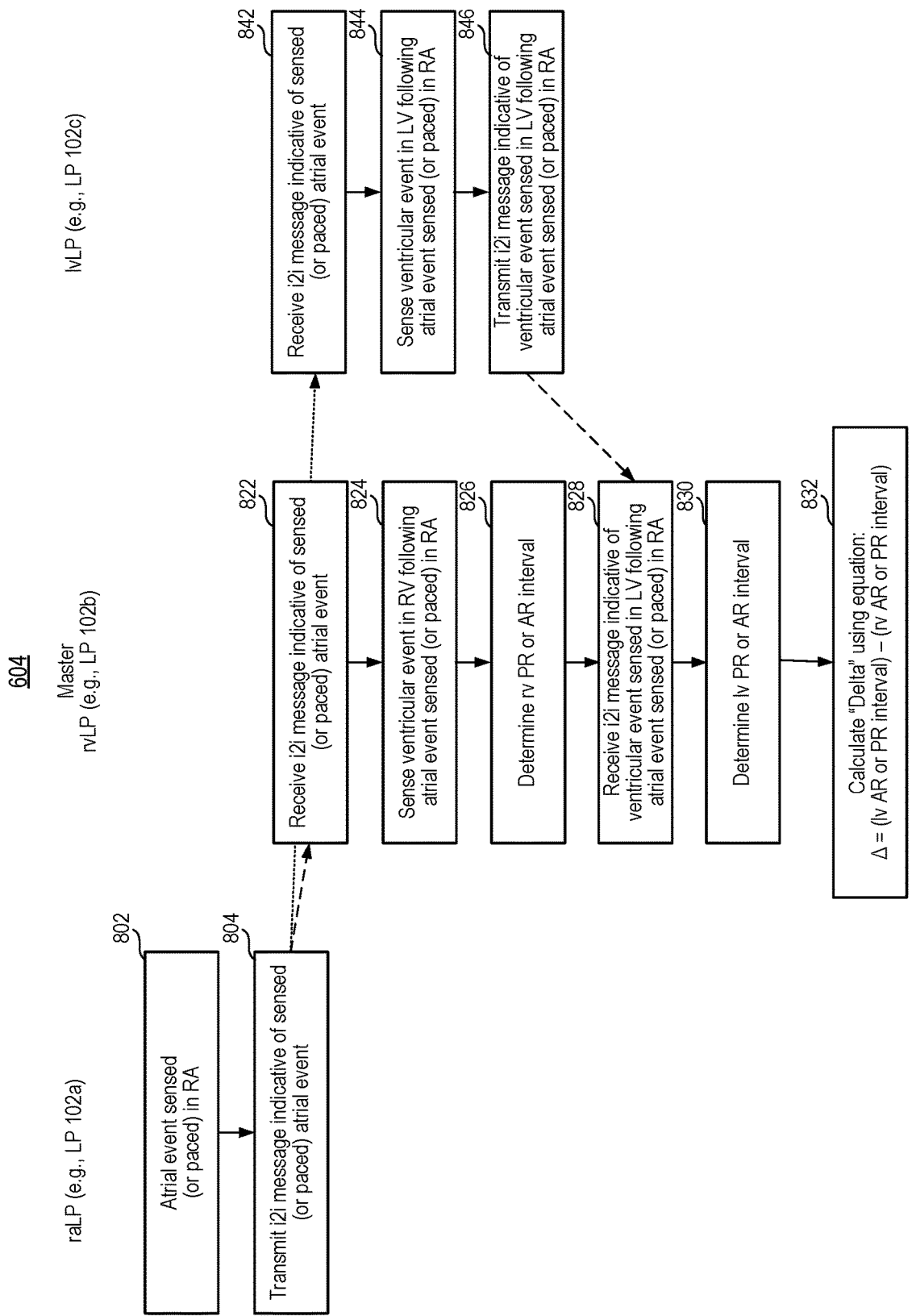
FIG. 8 is a flow diagram that is used to provide additional details of another one of the steps introduced in FIG. 6.
Figure 9:
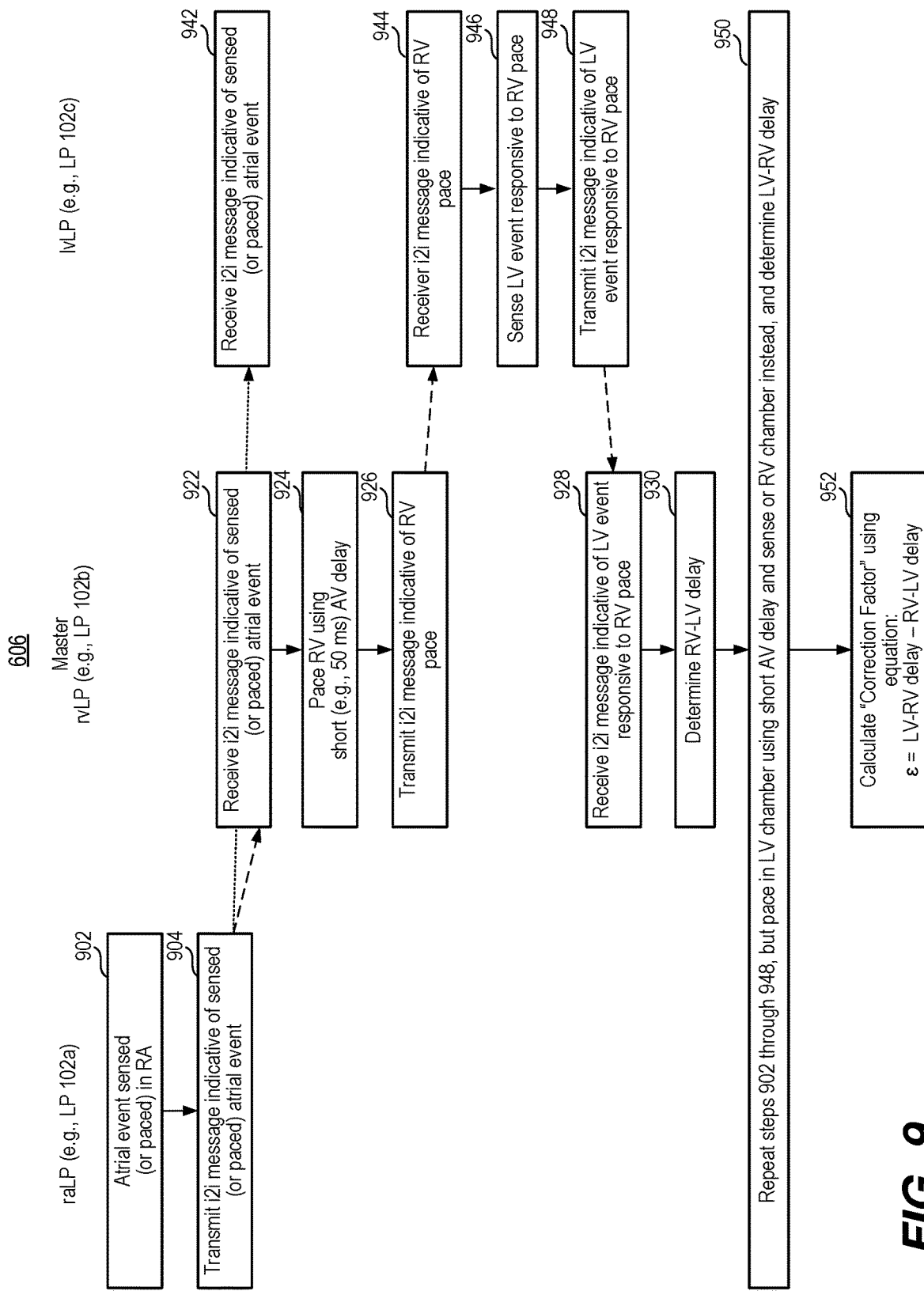
FIG. 9 is a flow diagram that is used to provide additional details of still another one of the steps introduced in FIG. 6.

Additional details of steps 602, 604, and 606, according to certain embodiments of the present technology, will now be described with reference to FIGS. 7, 8, and 9, respectively. In FIGS. 7A, 8, and 9, the steps shown along the left side of a page are steps that are performed by the raLP (e.g., the LP 102a in FIG. 1); the steps that are shown in the middle of a page are steps that are performed by the rvLP (e.g., the LP 102b in FIG. 1); and the steps that are shown along the right side of a page, if any, are performed by the lvLP (e.g., the LP 102c in FIG. 1).

Figure 7A:
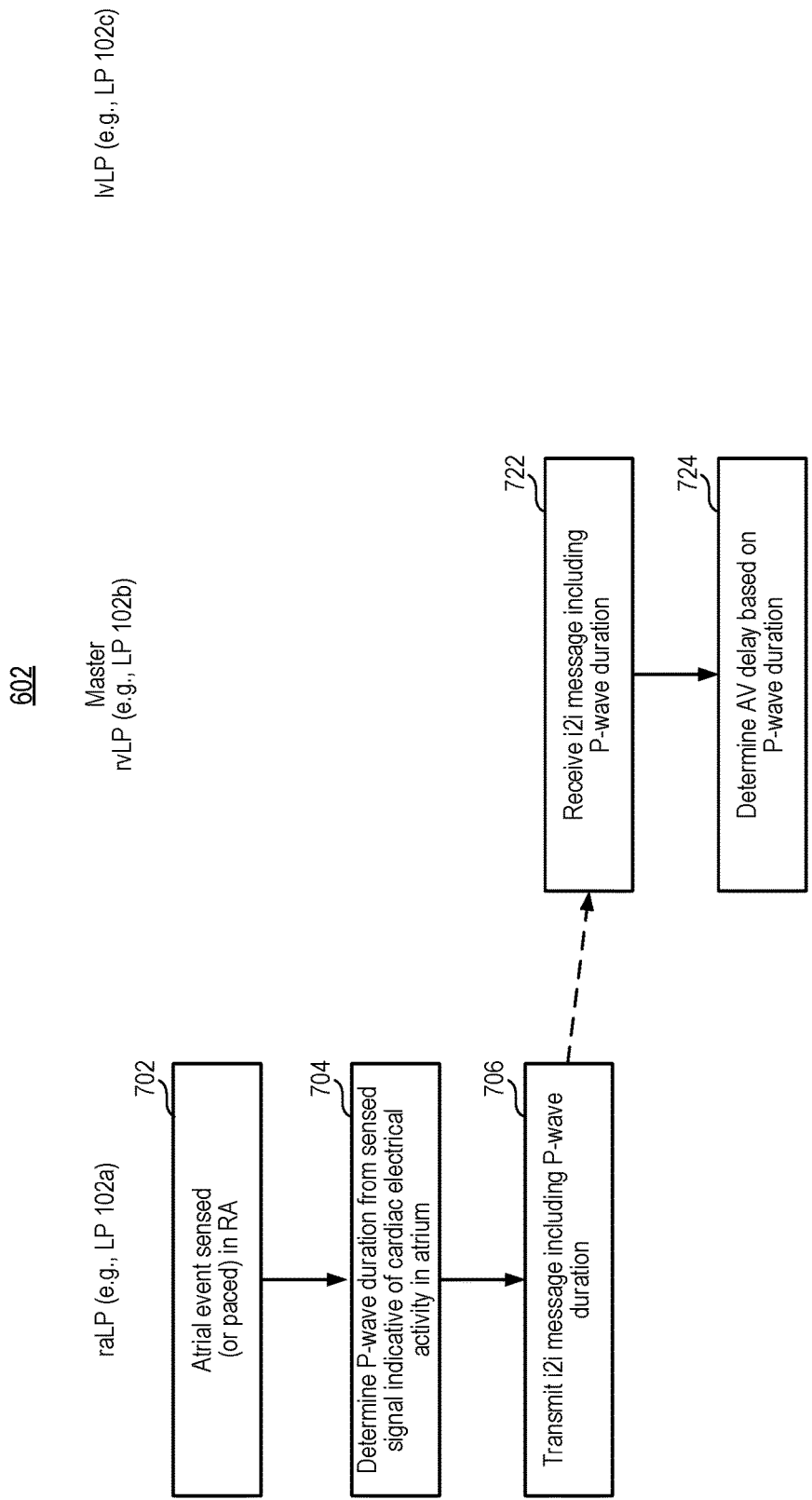
FIG. 7A is a flow diagram that is used to provide additional details of one of the steps introduced in FIG. 6.

Referring to FIG. 7A, which provides additional details for step 602 according to certain embodiments, step 702 involves the raLP (e.g., LP 102a) sensing or pacing an atrial event (i.e., an atrial depolarization). Step 704 involves the raLP determining a P-wave duration from a sensed signal (i.e., an electrogram) indicative of cardiac electrical activity in the atrium. The P-wave duration can be determined from a single cardiac cycle, i.e., from a single P-wave. Alternatively, and more preferably, the P-wave duration can be determined from a plurality of cardiac cycles, i.e., from a plurality of P-waves, e.g., by determining the mean or median of the plurality of P-waves.

Figures 7B, 7C:
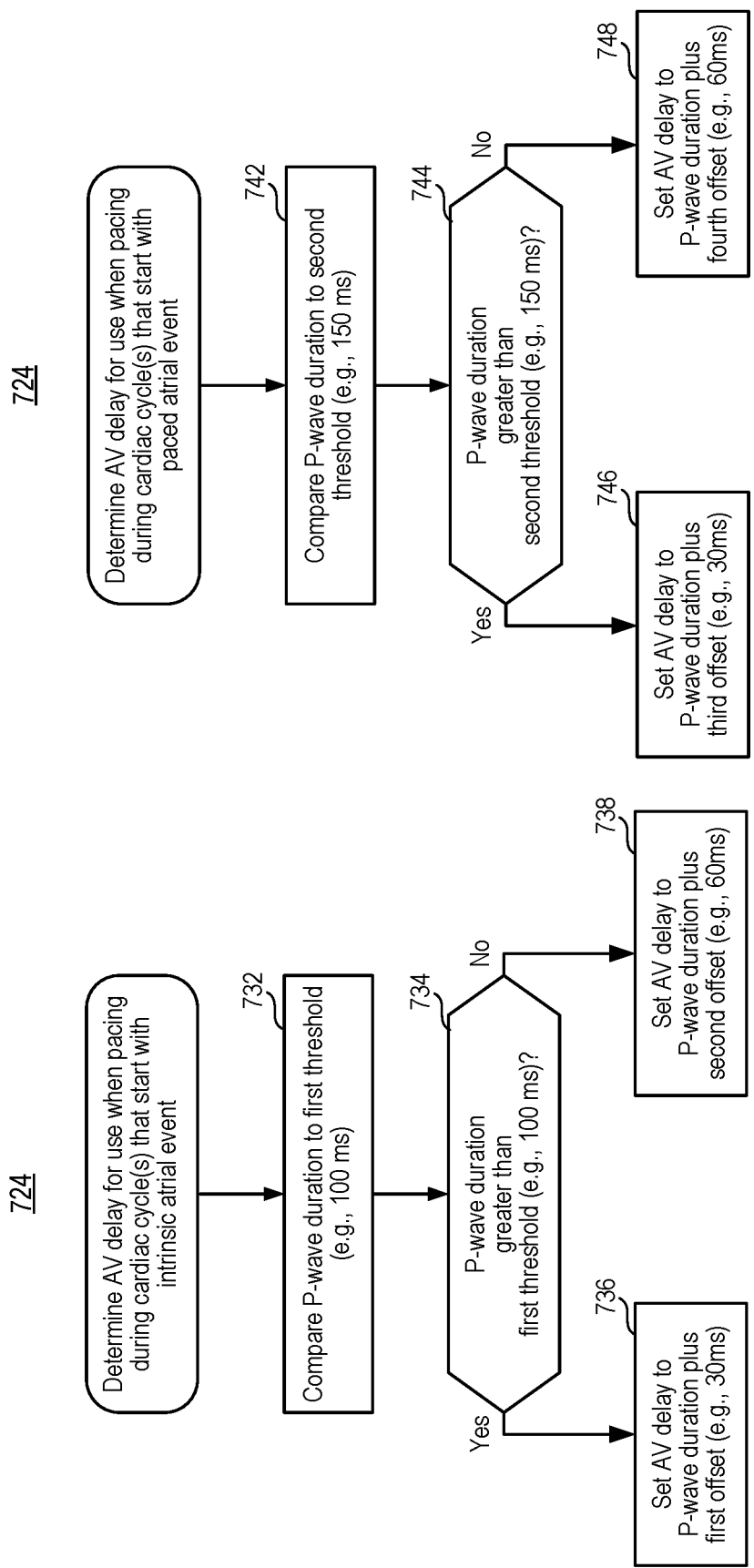
FIGS. 7B and 7C are flow diagrams that are used to provide additional details of one of the steps introduced in FIG. 7A.

Step 706 involves the raLP transmitting an i2i message to the master LP (e.g., the rvLP), wherein the i2i message includes the P-wave duration determined by the raLP. Step 722 involves the master LP (e.g., the rvLP) receiving the i2i message (from the raLP) that includes the P-wave duration. Step 724 involves the master LP (e.g., the rvLP) determining an AV delay based on the determined P-wave duration. FIGS. 7B and 7C provide additional details of how step 724 can be performed, and more specifically, how the AV delay can be determined based on the determined P-wave duration. The specific AV delay to use for CRT pacing will depend on whether the AV delay is for use in pacing during one or more cardiac cycles that start with an intrinsic atrial event, or the AV delay is for using in pacing during one or more cardiac cycles that start with a paced atrial event. Since it is unlikely to, be known beforehand whether a cardiac cycle will begin with an intrinsic or paced event, two types of AV delays can be determined at step 724, one AV delay for use when pacing during cardiac cycles that start with an intrinsic atrial event, and another AV delay for use when pacing during cardiac cycles that start with a paced atrial event. More specifically, the flow diagram in FIG. 7B illustrates how the AV delay can be determined when pacing starts with an intrinsic atrial event, and the flow diagram of FIG. 7C illustrates how the AV delay can be determined when pacing starts with a paced atrial event.

Referring to FIG. 7B, which illustrates how the AV delay can be determined when pacing starts with an intrinsic atrial event, at step 732 the P-wave duration is compared to a first threshold, and at step 734 there is a determination of whether the P-wave duration is greater than the first threshold. While shown as two separate steps, steps 732 and 734 can be combined into a single step. An example value for the first threshold is 100 ms, but the use of alternatively values for the first threshold are also possible and within the scope of the embodiments described herein. If the answer to the determination at step 734 is Yes (i.e., if the P-wave duration is greater than the first threshold), then at step 736 the AV delay is set to be equal to a sum of the P-wave duration plus a first offset (i.e., AV delay=P-wave duration+Offset$_1$). An example value for the first offset is 30 ms, but the use of alternatively values for the first offset are also possible and within the scope of the embodiments described herein. If the answer to the determination at step 734 is No (i.e., if the P-wave duration is not greater than the first threshold), then at step 738 the AV delay is set to be equal to a sum of the P-wave duration plus a second offset that is greater than the first offset (i.e., AV delay=P-wave duration+Offset$_2$). An example value for the second offset is 60 ms, but the use of alternatively values for the second offset are also possible and within the scope of the embodiments described herein.

Referring to FIG. 7C, which illustrates how the AV delay can be determined when pacing starts with a paced atrial event, at step 742 the P-wave duration is compared to a second threshold, which is greater than the first threshold, and at step 744 there is a determination of whether the P-wave duration is greater than the second threshold. The reason the second threshold is greater than the first threshold is because AR intervals are greater than PR intervals due to there being some delay between delivery of a pacing pulse and capture of the atrial chamber. While shown as two separate steps, steps 742 and 744 can be combined into a single step. An example value for the second threshold is 150 ms, but the use of alternatively values for the second threshold are also possible and within the scope of the embodiments described herein. If the answer to the determination at step 744 is Yes (i.e., if the P-wave duration is greater than the second threshold), then at step 736 the AV delay is set to be equal to a sum of the P-wave duration plus a third offset (i.e., AV delay=P-wave duration+Offset$_3$). An example value for the third offset is 30 ms, but the use of alternatively values for the third offset are also possible and within the scope of the embodiments described herein. If the answer to the determination at step 744 is No (i.e., if the P-wave duration is not greater than the second threshold), then at step 748 the AV delay is set to be equal to a sum of the P-wave duration plus a fourth offset that is greater than the third offset (i.e., AV delay=P-wave duration+Offset$_4$). An example value for the fourth offset is 60 ms, but the use of alternatively values for the fourth offset are also possible and within the scope of the embodiments described herein.

While it is preferable that the master LP performs a majority of the calculations and other determinations, such as determining the AV delay, it would also be possible for the raLP to determine the AV delay based on the P-wave duration, and then transmit the determined AV delay to the master LP in an i2i message. It is also noted that if the raLP is designated the master LP (e.g., rather than the rvLP being designated the master LP), then steps 706 and 722 would not be needed, and the raLP could both determine the P-wave duration and determine the AV delay based on the P-wave duration. It is also within the scope of the embodiments described herein to use some other measure of inter-atrial conduction delay (IACD), besides P-wave duration, to determine the AV delay.

FIG. 8 will now be used to describe additionally details of how the "delta" is determined at step 604, according to certain embodiments of the present technology. As noted above, the variable "delta" (Δ) represents an interventricular delay that is based an atrio-ventricular delay for the LV chamber and an atrio-ventricular delay for the RV chamber. Referring to FIG. 8, step 802 involves the raLP (e.g., LP 102a) sensing or pacing an atrial event (i.e., an atrial depolarization), and step 804 involves the raLP transmitting an i2i indicative of the sensed or paced atrial event. Where an atrial event (i.e., an atrial depolarization) is sensed at step 802, a time at which the atrial event is considered to occur can be, e.g., at a beginning, a peak, or an end of a P-wave, so long as the way step 802 is performed is consistent. The transmitted i2i message can be detected by the rvLP, as indicated at step 822, as well as by the lvLP, as indicated at step 842.

At step 824 the rvLP (e.g., 102b) senses a ventricular event in the RV chamber that follows that atrial event that is sensed or paced in the RA chamber at step 802, and at step 826 a right ventricular (rv) PR interval is determined (if the atrial event at step 802 was a sensed event), or a rv AR interval is determined (if the atrial event at step 802 was a paced event). Preferably, at steps 824 and 826, a time at which the ventricular event is considered to occur in the RV chamber is at a peak of an R-wave or QRS complex of an EGM indicative of electrical activity in the RV chamber.

At step 844 the lvLP (e.g., 102*c*) senses a ventricular event in the LV chamber that follows that atrial event that is sensed or paced in the RA chamber at step 802. For this discussion, it is presumed that the rvLP (e.g., 102*b*) is designated the master LP, in which case the lvLP (e.g., 102*c*), which is a slave, will transmit an i2i message indicative of the ventricular event sensed in the LV chamber following the atrial event sensed (or paced) in the RA chamber at step 802.

As indicated at step 828, the rvLP (e.g., 102*b*) receives the i2i message that was sent at step 846, and the rvLP at step 830 determines a left ventricular (lv) PR interval (if the atrial event at step 802 was a sensed event), or a lv AR interval (if the atrial event at step 802 was a paced event). Preferably, at steps 844 and 830, a time at which the ventricular event is considered to occur in the LV chamber is at a peak of an R-wave or QRS complex of an EGM indicative of electrical activity in the LV chamber.

At step 832, the master LP calculates the "delta" using the following equation:

$$\Delta = (lv\ AR\ \text{or}\ PR\ \text{interval}) - (rv\ AR\ \text{or}\ PR\ \text{interval}).$$

In other words, the "delta" is equal to the difference between the lv AR interval and the rv AR interval, or is equal to the difference between the lv PR interval and the rv PR interval. The flow diagram shown in FIG. 8 would be slightly changed if a different one of the LPs, other than the rvLP, was designated the master LP. As noted above, in the discussion of step 608 of FIG. 6, the master LP determines the VV delay based on as the "delta" ($\Delta$), as well as the "correction factor" epsilon ($\varepsilon$).

FIG. 9 will now be used to describe additionally details of how the "correction factor" is determined at step 606, according to certain embodiments of the present technology. Referring to FIG. 9, step 902 involves the raLP (e.g., LP 102*a*) sensing or pacing an atrial event (i.e., an atrial depolarization), and step 904 involves the raLP transmitting an i2i indicative of the sensed or paced atrial event. The transmitted i2i message can be detected by the rvLP, as indicated at step 922, as well as by the lvLP, as indicated at step 942.

At step 924 the rvLP (e.g., LP 102*b*) paces the RV chamber using a relatively short (e.g., 50 ms) AV delay, and the rvLP transmits an i2i message indicative of the RV pace being delivered. For example, such an i2i message can include a VP maker that provides a notification of a paced ventricular event.

At step 944 the i2i message (transmitted at step 926) is received by the lvLP (e.g., LP 102*c*), and at step 946 the lvLP senses an LV event (i.e., left ventricular depolarization) that is responsive to the RV pace. At step 948 the lvLP transmits an i2i message indicative of the LV event detected at step 946. For example, such an i2i message can include a VS marker that provides a notification of the sensed ventricular event.

At step 928 the rvLP, which is presumed to be the master LP, receives the i2i message (transmitted at step 948), and at step 930 the rvLP determines an RV-LV delay, which is the delay between when the paced RV event occurred at step 924 and when the sensed LV event occurred at step 946. In accordance with certain embodiments, a time at which a sensed event is considered to have occurred in the LV chamber is at a peak of an R-wave or QRS complex detected by lvLP implanted within the LV chamber.

As indicated at step 950 in FIG. 9, steps 902 through 948 are repeated, but pacing occurs in the LV chamber (by the lvLP) and sensing occurs in the RV chamber (by the rvLP) to thereby determine an LV-RV delay, which is the delay between when a paced LV event occurs and when a sensed RV event occurs. In accordance with certain embodiments, a time at which a sensed event is considered to have occurred in the RV chamber is at a peak of an R-wave or QRS complex detected by rvLP implanted within the RV chamber.

At step 952 the "correction factor" epsilon ($\varepsilon$) is determined using the following equation:

$$\varepsilon = LV\text{-}RV\ \text{delay} - RV\text{-}LV\ \text{delay}.$$

As noted above, in the discussion of step 608 of FIG. 6, the master LP determines the VV delay based on the "correction factor" epsilon ($\varepsilon$) as well as the "delta" ($\Delta\Delta$).

Referring back to the flow diagram of FIG. 6, the determining the P-wave duration at step 602 can occur during a first set of cardiac cycles that includes one or more cardiac cycles. If the first set of cardiac cycles includes a plurality of cardiac cycles (e.g., 10 cardiac cycles), then the P-wave duration can be the mean or median of the P-wave durations determined for the plurality of cardiac cycles.

Referring again to FIG. 8, the determining of the rv PR (or AR) interval at step 826 can occur during a second set of cardiac cycles that includes one or more cardiac cycles. If the second set of cardiac cycles includes a plurality of cardiac cycles (e.g., 10 cardiac cycles), then the rv PR (or AR) interval can be the mean or median of the rv PR (or AR) intervals determined for the plurality of cardiac cycles. Similarly, the determining of the lv PR (or AR) interval at step 830 can occur during a third set of cardiac cycles that includes one or more cardiac cycles. If the third set of cardiac cycles includes a plurality of cardiac cycles (e.g., 10 cardiac cycles), then the lv PR (or AR) interval can be the mean or median of the lv PR (or AR) intervals determined for the plurality of cardiac cycles. Depending upon implementation, cardiac cycles including in the second and third sets of cardiac cycles, may, or may not, overlap one another, and may, or may not, overlap with the first set of cardiac cycles that is used to determine the P-wave duration.

Referring again to FIG. 9, the pacing the RV chamber and the determining the RV-LV delay at steps 924 through 930 can occur during a fourth set of cardiac cycles that includes one or more cardiac cycles. If the fourth set of cardiac cycles includes a plurality of cardiac cycles (e.g., 10 cardiac cycles), then the RV-LV delay determined at step 930 can be the mean or median of the RV-LV delays determined for the plurality of cardiac cycles that do not overlap with any of the first, second, and third sets of cardiac cycles. Still referring to FIG. 9, the pacing the LV chamber and the determining the LV-RV delay (as indicated at step 950) can occur during a fifth set of cardiac cycles include one or more cardiac cycles that do not overlap with any of the first, second, third, and fourth sets of cardiac cycles.

Figure 10:
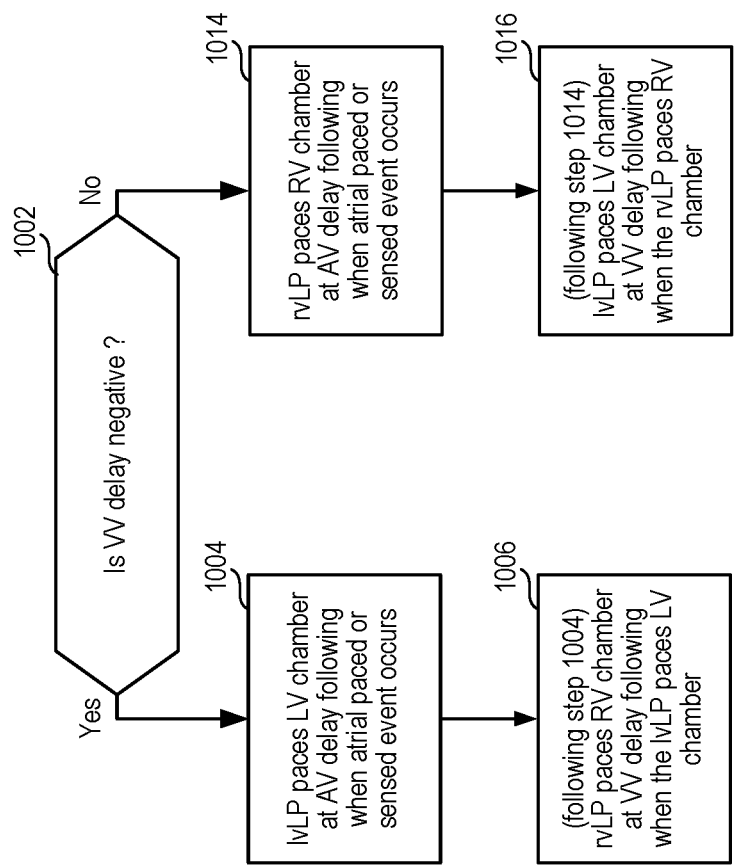
FIG. 10 is a flow diagram that is used to provide additional details of a further one of the steps introduced in FIG. 6.

FIG. 10 is now used to describe certain embodiments in which the raLP, rvLP, and lvLP collectively perform CRT using the AV delay determined at step 602 and the VV delay determined at step 608. The steps described with reference to FIG. 10 can be part of the pacing orchestrated by the master LP at step 610 in FIG. 6.

Referring to FIG. 10, at step 1002 there is a determination of whether the VV delay, that was determined at step 608, is negative. If the answer to the determination at step 1002 is Yes (i.e., if the VV delay is negative), then flow goes to step 1004. If the answer to the determination at step 1002 is No (i.e., if the VV delay is positive), then flow goes to step 1014. Prior to step 1002, or between steps 1002 and 1004 (or 1014), the rvLP (e.g., 102*b*) determines on its own (e.g., based on a far-field signal) or based on an i2i message received from the raLP (e.g., 102a), when an atrial paced or sensed event occurs. Similarly, the lvLP (e.g., 102c) also determines on its own (e.g., based on a far-field signal or a sensor signal) or based on an i2i message received from the raLP (e.g., 102a), when the atrial paced or sensed event occurs.

If the VV delay is negative, then at step 1004 the lvLP paces the LV chamber at the AV delay (determined at step 602) following when the atrial paced or sensed event occurs. Thereafter at step 1006 the rvLP paces the RV chamber at the VV delay (determined at step 608) following when the lvLP paces the LV chamber (at step 1004). Explained another way, at step 1006 the rvLP paces the RV chamber at a delay=AV delay+VV delay, following when the atrial paced or sensed event occurs. If the VV delay is positive, then at step 1014 the rvLP paces the RV chamber at the AV delay (determined at step 602) following when the atrial paced or sensed event occurs. Thereafter, at step 1016, the lvLP paces the LV chamber at the VV delay (determined at step 608) following when the rvLP paces the RV chamber (at step 1014). Explained another way, at step 1016 the lvLP paces the LV chamber at a delay=AV delay+VV delay, following when the atrial paced or sensed event occurs.

In accordance with certain embodiments, following pacing in the RV and LV chambers, by the rvLP and lvLP (e.g., 102b and 102c), the raLP (e.g., 102a) paces the RA chamber at a VA delay following when one of the RV or LV chambers is paced. The VA delay that is used by the raLP can be preprogrammed and fixed, or may be rate dependent, depending on how the raLP is programmed and/or set. The raLP can determine when the RV and/or LP chambers were paced based on a far-field signal detected by the raLP (e.g., 102a), based on a sensor signal (e.g., heart sound signal) detected by the raLP, or based on one or more transmitted i2i message the raLP receives from one or both of the rvLP and/or the lvLP (e.g., 102b and/or 102c).

Figure 11:
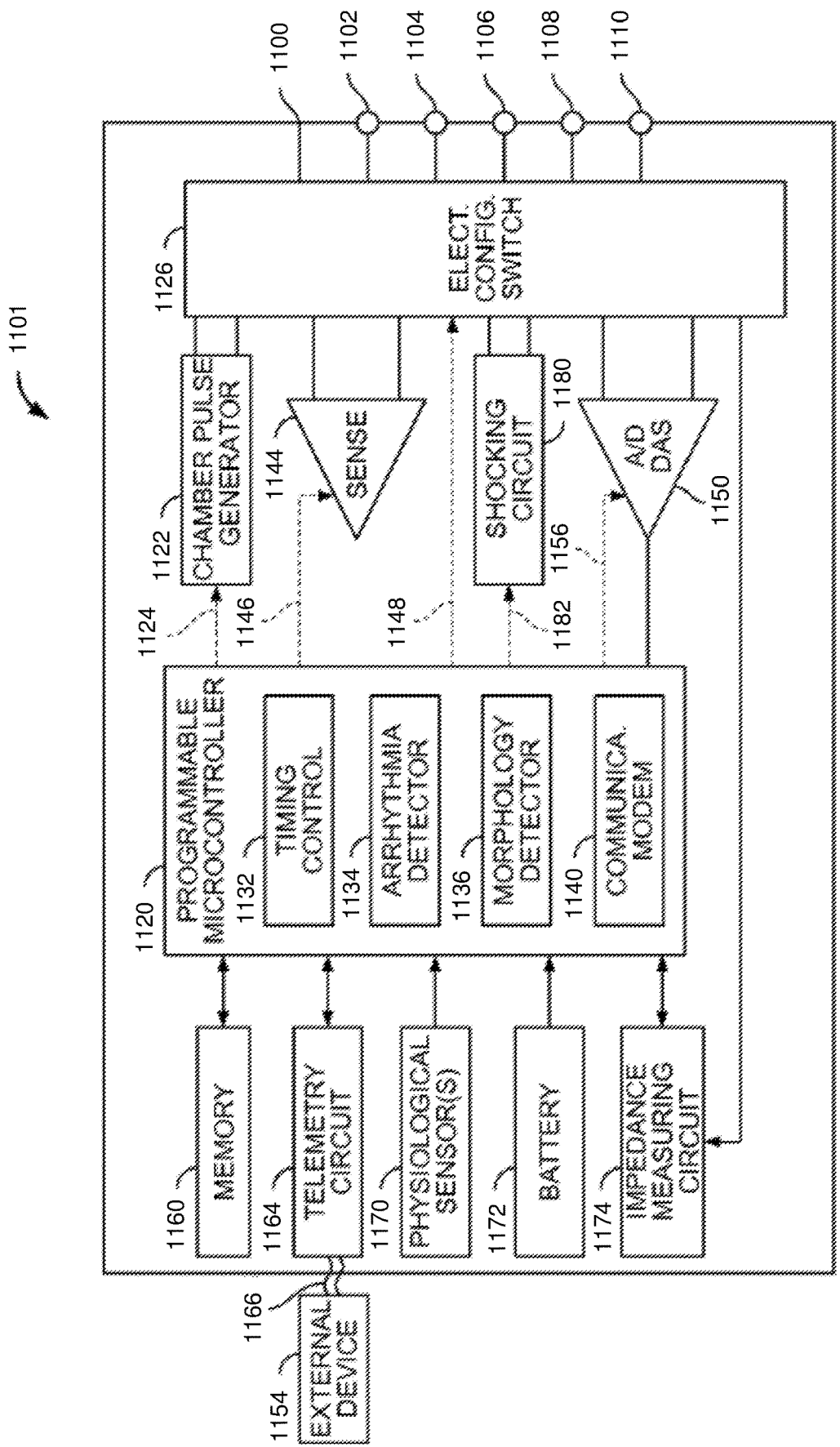
FIG. 11 shows a block diagram of an embodiment of an LP that is implanted into a patient as part of an implantable cardiac system in accordance with certain embodiments herein.

FIG. 11 shows a block diagram of showing exemplary further details of an LP 1101 (e.g., 102, 102', or 102") that is implanted into the patient as part of the implantable cardiac system that performs CRT in accordance with certain embodiments herein. The LP 1101 has a housing 1100 to hold the electronic/computing components. Housing 1100 (which is often referred to as the "can", "case", "encasing", or "case electrode") may be programmably selected to act as the return electrode for certain stimulus modes. Housing 1100 may further include a connector (not shown) with a plurality of terminals 1102, 1104, 1106, 1108, and 1110. The terminals may be connected to electrodes that are located in various locations on housing 1100 or elsewhere within and about the heart. LP 1101 includes a programmable microcontroller 1120 that controls various operations of LP 1101, including cardiac monitoring and stimulation therapy. Microcontroller 1120 includes a microprocessor (or equivalent control circuitry), RAM and/or ROM memory, logic and timing circuitry, state machine circuitry, and I/O circuitry. The microcontroller is an example of a controller (e.g., 112) discussed above.

LP 1101 further includes a pulse generator 1122 that generates stimulation pulses and communication pulses for delivery by one or more electrodes coupled thereto. Pulse generator 1122 is controlled by microcontroller 1120 via control signal 1124. Pulse generator 1122 may be coupled to the select electrode(s) via an electrode configuration switch 1126, which includes multiple switches for connecting the desired electrodes to the appropriate I/O circuits, thereby facilitating electrode programmability. Switch 1126 is controlled by a control signal 1128 from microcontroller 1120.

In FIG. 11, a single pulse generator 1122 is illustrated. Optionally, the LP may include multiple pulse generators, similar to pulse generator 1122, where each pulse generator is coupled to one or more electrodes and controlled by microcontroller 1120 to deliver select stimulus pulse(s) to the corresponding one or more electrodes. For example, one pulse generator can be used to generate pacing pulses, and another pulse generator can be used to generate i2i pulses.

Microcontroller 1120 is illustrated as including timing control circuitry 1132 to control the timing of the stimulation pulses (e.g., pacing rate, atrio-ventricular (AV) delay, atrial interconduction (A-A) delay, or ventricular interconduction (V-V) delay, etc.). Timing control circuitry 1132 may also be used for the timing of refractory periods, blanking intervals, noise detection windows, evoked response windows, alert intervals, marker channel timing, and so on. Microcontroller 1120 may also have an arrhythmia detector 1134 for detecting arrhythmia conditions and a morphology detector 1136. Although not shown, the microcontroller 1120 may further include other dedicated circuitry and/or firmware/software components that assist in, monitoring various conditions of the patient's heart and managing pacing therapies. The microcontroller can include a processor. The microcontroller, and/or the processor thereof, can be used to perform the methods of the present technology described herein.

LP 1101 is further equipped with a communication modem (modulator/demodulator) 1140 to enable wireless communication with the remote slave pacing unit. Modem 1140 may include one or more transmitters and one or more receivers as discussed herein in connection with FIG. 1B. In one implementation, modem 1140 may use low or high frequency modulation. As one example, modem 1140 may transmit i2i messages and other signals through conductive communication between a pair of electrodes. Modem 1140 may be implemented in hardware as part of microcontroller 1120, or as software/firmware instructions programmed into and executed by microcontroller 1120. Alternatively, modem 1140 may reside separately from the microcontroller as a standalone component.

LP 1101 includes a sensing circuit 1144 selectively coupled to one or more electrodes, that perform sensing operations, through switch 1126 to detect the presence of cardiac activity associated with one or more chambers of the heart. Sensing circuit 1144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 1126 determines the sensing polarity of the cardiac signal by selectively closing the appropriate switches. In this way, the clinician may program the sensing polarity independent of the stimulation polarity.

The output of sensing circuit 1144 is connected to microcontroller 1120 which, in turn, triggers or inhibits the pulse generator 1122 in response to the presence or absence of cardiac activity. Sensing circuit 1144 receives a control signal 1146 from microcontroller 1120 for purposes of controlling the gain, threshold, polarization charge removal circuitry (not shown), and the timing of any blocking circuitry (not shown) coupled to the inputs of the sensing circuitry.

In FIG. 11, a single sensing circuit 1144 is illustrated. Optionally, the LP may include multiple sensing circuits, similar to sensing circuit 1144, where each sensing circuit is coupled to one or more electrodes and controlled by microcontroller 1120 to sense electrical activity detected at the corresponding one or more electrodes. For example, one sensing circuit can be used to sense near-field signals, another sensing circuit can be used to sense far-field signals, and one or more further sensing circuits can be used to sense i2i signals.

LP 1101 further includes an analog-to-digital (A/D) data acquisition system (DAS) 1150 coupled to one or more electrodes via switch 1126 to sample cardiac signals across any pair of desired electrodes. Data acquisition system 1150 is configured to acquire intracardiac electrogram signals, convert the raw analog data into digital data, and store the digital data for later processing and/or telemetric transmission to an external device 1154 (e.g., a programmer, local transceiver, or a diagnostic system analyzer). Data acquisition system 1150 is controlled by a control signal 1156 from the microcontroller 1120.

Microcontroller 1120 is coupled to a memory 1160 by a suitable data/address bus. The programmable operating parameters used by microcontroller 1120 are stored in memory 1160 and used to customize the operation of LP 1101 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of LP 1101 may be non-invasively programmed into memory 1160 through a telemetry circuit 1164 in telemetric communication via communication link 1166 with external device 1154. Telemetry circuit 1164 allows intracardiac electrograms and status information relating to the operation of LP 1101 (as contained in microcontroller 1120 or memory 1160) to be sent to external device 1154 through communication link 1166.

LP 1101 can further include magnet detection circuitry (not shown), coupled to microcontroller 1120, to detect when a magnet is placed over the unit. A magnet may be used by a clinician to perform various test functions of LP 1101 and/or to signal microcontroller 1120 that external device 1154 is in place to receive or transmit data to microcontroller 1120 through telemetry circuits 1164.

LP 1101 can further include one or more physiological sensors 1170. Such sensors are commonly referred to as "rate-responsive" sensors because they are typically used to adjust pacing stimulation rates according to the exercise state of the patient. However, physiological sensor 1170 may further be used to detect changes in cardiac output, changes in the physiological condition of the heart, or diurnal changes in activity (e.g., detecting sleep and wake states). Signals generated by physiological sensors 1170 are passed to microcontroller 1120 for analysis. Microcontroller 1120 responds by adjusting the various pacing parameters (such as rate, AV Delay, VN Delay, etc.) at which the atrial and ventricular pacing pulses are administered. While shown as being included within LP 1101, physiological sensor(s) 1170 may be external to LP 1101, yet still be implanted within or carried by the patient. Examples of physiologic sensors might include sensors that, for example, sense temperature, respiration rate, pH of blood, ventricular gradient, activity, position/posture, minute ventilation (MV), and so forth. The physiological sensors 1170 can include, e.g., an accelerometer (e.g., 154 in FIG. 1B) and/or a pressure sensor (e.g., 156 in FIG. 1B).

A battery 1172 provides operating power to all of the components in LP 1101. Battery 1172 is preferably capable of operating at low current drains for long periods of time. Battery 1172 also desirably has a predictable discharge characteristic so that elective replacement time can be detected. As one example, LP 1101 employs a lithium carbon monofluoride (Li—CFx) battery. In certain embodiments, examples of which were described above with reference to FIGS. 9A and 9B, the battery 1172 (which was labeled 924 in FIGS. 9A and 9B) can be located in a first hermetic electrically conductive housing, and the microcontroller 1120 and other circuitry can be located in a second hermetic electrically conductive housing.

LP 1101 further includes an impedance measuring circuit 1174, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. Impedance measuring circuit 1174 is coupled to switch 1126 so that any desired electrode may be used. In this embodiment LP 1101 further includes a shocking circuit 1180 coupled to microcontroller 1120 by a data/address bus 1182.

187 In some embodiments, an LP is configured to be implantable in any chamber of the heart, namely either atrium (RA, LA) or either ventricle (RV, LV), or alternatively, in a specific cardiac chamber. Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking & refractory periods, etc. Accordingly, each LP needs to know an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or VVI), and for the IPG to utilize the proper set of settings and algorithms (e.g., V-AutoCapture vs ACap-Confirm, sensing sensitivities, etc.).

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 6-10. For another example, it is possible to change the boundaries of some of the dashed blocks shown in FIGS. 1B and 11.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for performing cardiac resynchronization therapy (CRT) using an implantable leadless pacemaker system including a first leadless pacemaker (LP1) implanted in or on a right atrial (RA) chamber, a second leadless pacemaker (LP2) implanted in or on a right ventricular (RV) chamber, and a third leadless pacemaker (LP3) implanted in or on a left ventricular (LV) chamber, wherein one of the LP1, the LP2, or the LP3 is designated a master LP, the method comprising:
   (a) the LP1, which is implanted in or on the RA chamber, measuring a P-wave duration based on a signal sensed by the LP1;
   (b) the LP1, which is implanted in or on the RA chamber, or another one of the LPs that is designated the master LP, determining an atrio-ventricular (AV) delay based on the measured P-wave duration;
   (c) the LP2, which is implanted in or on the RV chamber, or another one of the LPs that is designated the master LP, determining a first AR or PR interval indicative of a time between an atrial depolarization and a ventricular depolarization in the RV chamber;
   (d) the LP3, which is implanted in or on the LV chamber, or another one of the LPs that is designated the master LP, determining a second AR or PR interval indicative of a time between an atrial depolarization and a ventricular depolarization in the LV chamber;
   (e) the one of the LPs that is designated the master LP determining a delta indicative of a difference between the first AR or PR interval and the second AR or PR interval;
   (f) the LP2, which is implanted in or on the RV chamber, pacing the RV chamber, and at least one of the LPs determining an RV-LV delay indicative of a time it takes for a ventricular depolarization in the RV chamber to propagate to the LV chamber;
   (g) the LP3, which is implanted in or on the LV chamber, pacing the LV chamber, and at least one of the LPs determining an LV-RV delay indicative of a time it takes for a ventricular depolarization in the LV chamber to propagate to the RV chamber;
   (h) the one of the LPs that is designated the master LP determining a correction factor indicative of a difference between the LV-RV delay and the RV-LV delay;
   (i) the one of the LPs that is designated the master LP determining a VV delay based on the determined delta and the determined correction factor; and
   (j) the LP1, the LP2, and the LP3 collectively performing CRT using the determined AV delay and the determined VV delay.

2. The method of claim 1, wherein:
the measuring the P-wave duration at step (a) occurs during a first set of cardiac cycles comprising one or more cardiac cycles;
the determining the first AR or PR interval at step (c) occurs during a second set of cardiac cycles comprising one or more cardiac cycles that may or may not overlap with the first set of cardiac cycles;
the determining the second AR or PR interval at step (d) occurs during a third set of cardiac cycles comprising one or more cardiac cycles that may or may not overlap with the first and/or second set of cardiac cycles;
the pacing the RV chamber and the determining the RV-LV delay at step (f) occurs during a fourth set of cardiac cycles comprising one or more cardiac cycles that do not overlap with any of the first, second, and third sets of cardiac cycles; and
the pacing the LV chamber and the determining the LV-RV delay at step (g) occurs during a fifth set of cardiac cycles comprising one or more cardiac cycles that do not overlap with any of the first, second, third, and fourth sets of cardiac cycles.

3. The method of claim 1, wherein when the AV delay is for use in pacing during one or more cardiac cycles that start with an intrinsic atrial event, the determining the AV delay based on the measured P-wave duration, comprises:
setting the AV delay to the P-wave duration plus a first offset, in response to the P-wave duration being greater than a threshold duration; and setting the AV delay to the P-wave duration plus a second offset that is greater than the first offset, in response to the P-wave duration being less than the threshold duration.

4. The method of claim 3, wherein when the AV delay is for use in pacing during one or more cardiac cycles that start with a paced atrial event, the determining the AV delay based on the measured P-wave duration, comprises:
  setting the AV delay to the P-wave duration plus a third offset, in response to the P-wave duration being greater than a second threshold duration; and
  setting the AV delay to the P-wave duration plus a fourth offset that is greater than the third offset, in response to the P-wave duration being less than the second threshold duration.

5. The method of claim 1, wherein at step (i) the one of the LPs that is designated the master LP determining the VV delay based on the determined delta and the determined correction factor, comprises:
  the one of the LPs that is designated the master LP determining the VV delay as being equal to half of a sum of the determined delta plus the determined correction factor.

6. The method of claim 1, wherein at step (j) the LP1, the LP2, and the LP3 collectively performing CRT using the determined AV delay and the determined VV delay, comprises:
  the LP2, determining on its own or based on an i2i message received from the LP1, when an atrial paced or sensed event occurs; and
  the LP3, determining on its own or based on an i2i message received from the LP1, when the atrial paced or sensed event occurs;
  if the VV delay is negative, then the LP3 pacing the LV chamber at the AV delay following when the atrial paced or sensed event occurs, and then the LP2 pacing the RV chamber at the VV delay following when the LP3 paces the LV chamber; and
  if the VV delay is positive, then the LP2 pacing the RV chamber at the AV delay following when the atrial paced or sensed event occurs, and then the LP3 pacing the LV chamber at the VV delay following when the LP2 paces the RV chamber.

7. The method of claim 1, wherein at step (j) the LP1, the LP2, and the LP3 collectively performing CRT using the determined AV delay and the determined VV delay, comprises:
  the LP2, determining on its own or based on an i2i message received from the LP1, when an atrial paced or sensed event occurs; and
  the LP3, determining on its own or based on an i2i message received from the LP1, when the atrial paced or sensed event occurs;
  if the VV delay is negative, then the LP3 pacing the LV chamber at the AV delay following when the atrial paced or sensed event occurs, and then the LP2 pacing the RV chamber at a delay equal to a sum of the AV delay plus the VV delay following when the atrial paced or sensed event occurs; and
  if the VV delay is positive, then the LP2 pacing the RV chamber at the AV delay following when the atrial paced or sensed event occurs, and then the LP3 pacing the LV chamber at the delay equal to a sum of the AV delay plus the VV delay following when the atrial paced or sensed event occurs.

8. The method of claim 1, wherein at step (j) the LP1, the LP2, and the LP3 collectively performing CRT, using the determined AV delay and the determined VV delay, is orchestrated by the one of the LPs that is designated the master LP.

9. The method of claim 1, wherein at step (j) the LP1, the LP2, and the LP3 collectively performing CRT, includes the LP1 pacing the RA chamber at a VA delay following when the LP2 paced the RV chamber or the LP3 paced the LV chamber.

10. The method of claim 1, wherein the LP2, which is implanted in or on the RV chamber, is designated the master LP.

11. An implantable system for performing cardiac resynchronization therapy (CRT), comprising:
  a first leadless pacemaker (LP1) configured to be implanted in or on a right atrial (RA) chamber and selectively pace the RA chamber;
  a second leadless pacemaker (LP2) configured to be implanted in or on a right ventricular (RV) chamber and selectively pace the RV chamber;
  a third leadless pacemaker (LP3) configured to be implanted in or on a left ventricular (LV) chamber and selectively pace the LV chamber;
  one of the LP1, the LP2, or the LP3 designated a master LP;
  the LP1 also configured to sense a signal and measure a P-wave duration based on the signal sensed by the LP1;
  the LPI, or another one of the LPs that is designated the master LP, configured to determine an atrio-ventricular (AV) delay based on the measured P-wave duration;
  the LP2, or another one of the LPs that is designated the master LP, configured to determine a first AR or PR interval indicative of a time between an atrial depolarization and a ventricular depolarization in the RV chamber;
  the LP3, or another one of the LPs that is designated the master LP, configured to determine a second AR or PR interval indicative of a time between an atrial depolarization and a ventricular depolarization in the LV chamber;
  at least one of the LPs configured to determine an RV-LV delay indicative of a time it takes for a ventricular depolarization in the RV chamber to propagate to the LV chamber in response to the LP2 pacing the RV chamber;
  at east one of the LPs configured to determine an LV-RV delay indicative of a time it takes for a ventricular depolarization in the LV chamber to propagate to the RV chamber in response to the LP3 pacing the LV chamber; and
  the one of the LPs that is designated the master LP configured to determine a delta indicative of a difference between the first AR or PR interval and the second AR or PR interval, determine a correction factor indicative of a difference between the LV-RV delay and the RV-LV delay, and determine a VV delay based on the determined delta and the determined correction factor;
  wherein the LP1, the LP2, and the LP3 are configured to collectively perform CRT using the determined AV delay and the determined VV delay.

12. The system of claim 11, wherein:
  the LP1, which is configured to be implanted in or on the RA chamber, is configured to measure the P-wave duration during a first set of cardiac cycles comprising one or more cardiac cycles;
  the LP2, which is configured to be implanted in or on the RV chamber, is configured to determine the first AR or PR interval during a second set of cardiac cycles comprising one or more cardiac cycles that may or may not overlap with the first set of cardiac cycles;

the LP3, which is configured to be implanted in or on the LV chamber, is configured to determine the second AR or PR interval during a third set of cardiac cycles comprising one or more cardiac cycles that may or may not overlap with the first and/or second set of cardiac cycles;

the LP2 is also configured to determine the RV-LV delay during a fourth set of cardiac cycles comprising one or more cardiac cycles that do not overlap with any of the first, second, and third sets of cardiac cycles; and the LP3 is also configured to determine the LV-RV delay during a fifth set of cardiac cycles comprising one or more cardiac cycles that do not overlap with any of the first, second, third, and fourth sets of cardiac cycles.

13. The system of claim 11, wherein when the AV delay is for use in pacing during one or more cardiac cycles that start with an intrinsic atrial event, the LP that is designated the master is configured to:

set the AV delay to the P-wave duration plus a first offset, in response to the P-wave duration being greater than a threshold duration; and set the AV delay to the P-wave duration plus a second offset that is greater than the first offset, in response to the P-wave duration being less than the threshold duration.

14. The system of claim 13, wherein when the AV delay is for use in pacing during one or more cardiac cycles that start with a paced atrial event, the LP that is designated the master is configured to:

set the AV delay to the P-wave duration plus a third offset, in response to the P-wave duration being greater than a second threshold duration; and set the AV delay to the P-wave duration plus a fourth offset that is greater than the third offset, in response to the P-wave duration being less than the second threshold duration.

15. The system of claim 11, wherein the LP that is designated the master LP is configured to determine the VV delay as being equal to half of a sum of the determined delta plus the determined correction factor.

16. The system of claim 11, wherein the LP1, the LP2, and the LP3 are configured to collectively performing CRT using the determined AV delay and the determined VV delay, and wherein:

the LP2 is configured to determine on its own or based on an i2i message received from the LP1, when an atrial paced or sensed event occurs; and the LP3 is configured to determine on its own or based on an i2i message received from the LP1, when the atrial paced or sensed event occurs;

when the VV delay is negative, the LP3 is configured to pace the LV chamber at the AV delay following when the atrial paced or sensed event occurs, and the LP2 is configured to pace the RV chamber at the VV delay following when the LP3 paces the LV chamber; and when the VV delay is positive, the LP2 is configured to pace the RV chamber at the AV delay following when the atrial paced or sensed event occurs, and the LP3 is configured to pace the LV chamber at the VV delay following when the LP2 paces the RV chamber.

17. The system of claim 11, wherein the LP1, the LP2, and the LP3 are configured to collectively performing CRT using the determined AV delay and the determined VV delay, and wherein:

the LP2, which is configured to be implanted in or on the RV chamber, is configured to determine on its own or based on an i2i message received from the LP1, when an atrial paced or sensed event occurs; and the LP3, which is configured to be implanted in or on the LV chamber, is configured to determine on its own or based on an i2i message received from the LP1, when the atrial paced or sensed event occurs;

when the VV delay is negative, the LP3 is configured to pace the LV chamber at the AV delay following when the atrial paced or sensed event occurs, and the LP2 is configured to pace the RV chamber at a delay equal to a sum of the AV delay plus the VV delay following when the atrial paced or sensed event occurs; and when the VV delay is positive, the LP2 is configured to pace the RV chamber at the AV delay following when the atrial paced or sensed event occurs, and the LP3 is configured to pace the LV chamber at the delay equal to a sum of the AV delay plus the VV delay following when the atrial paced or sensed event occurs.

18. The system of claim 11, the one of the LPs that is designated the master LP is configured to orchestrate the CRT that is collectively performed by the LP1, the LP2, and the LP3 using the determined AV delay and the determined VV delay.

19. The system of claim 11, wherein the LP1, which is configured to be implanted in or on the RA chamber, is configured to pace the RA chamber at a VA delay following when the LP2 paces the RV chamber or the LP3 paces the LV chamber.

20. The system of claim 11, wherein the LP2, which is configured to be implanted in or on the RV chamber, is designated the master LP.

21. A leadless pacemaker (rvLP) configured to be implanted in or on a right ventricular (RV) chamber and configured to perform cardiac resynchronization therapy (CRT) along with a leadless pacemaker (raLP) configured to be implanted in or on a right atrial (RA) chamber and a leadless pacemaker (lvLP) configured to be implanted in or on a left ventricular (LV) chamber, the rvLP comprising:

one or more pulse generators configured to selectively produce pacing pulses and implant-to-implant (i2i) communication pulses, the pacing pulses for use in pacing the RV chamber, and the i2i communication pulses for use in sending i2i messages to at least one of the raLP or the lvLP;

a plurality of electrodes at least two of which can be used to deliver one or more pacing pulses to the RV chamber, at least two of which can be used to transmit and receive one or more i2i communication pulses to and from at least one of the raLP or the lvLP, and at least two of which can be used to sense a far-field signal from which cardiac activity associated with at least one of the RA or LV chambers may be detected; and a controller configured to determine an atrio-ventricular (AV) delay based on a P-wave duration measurement received via one or more i2i communication pulses from the raLP;

an RV-LV delay indicative of a time it takes for a ventricular depolarization in the RV chamber to propagate to the LV chamber in response to the rvLP pacing the RV chamber;

an LV-RV delay indicative of a time it takes for a ventricular depolarization in the LV chamber to propagate to the RV chamber in response to the lvLP pacing the LV chamber;

a delta indicative of a difference between a first AR or PR interval and a second AR or PR interval, the first AR or PR interval indicative of a time between an atrial depolarization and a ventricular depolarization in the RV chamber, and the second AR or PR interval indicative of a time between an atrial depolarization and a ventricular depolarization in the LV chamber;

a correction factor indicative of a difference between the LV-RV delay and the RV-LV delay; and a VV delay based on the determined delta and the determined correction factor;

the controller also configured to coordinate performance of CRT collectively by the rvLP, raLP, and lvLP using the determined AV delay and the determined VV delay.

* * * * *